(12) United States Patent
Lopez et al.

(10) Patent No.: US 8,758,306 B2
(45) Date of Patent: Jun. 24, 2014

(54) MEDICAL CONNECTORS AND METHODS OF USE

(75) Inventors: George A. Lopez, Laguna Beach, CA (US); Thomas F. Fangrow, Jr., Mission Viejo, CA (US); Bob Foret, Highland, UT (US)

(73) Assignee: ICU Medical, Inc., San Clemente, CA (US)

(*) Notice: Subject to any disclaimer, the term of this patent is extended or adjusted under 35 U.S.C. 154(b) by 405 days.

(21) Appl. No.: 13/106,781

(22) Filed: May 12, 2011

(65) Prior Publication Data

US 2011/0282302 A1    Nov. 17, 2011

Related U.S. Application Data

(60) Provisional application No. 61/345,554, filed on May 17, 2010, provisional application No. 61/392,426, filed on Oct. 12, 2010.

(51) Int. Cl.
*A61M 5/00* (2006.01)
*A61M 39/00* (2006.01)

(52) U.S. Cl.
USPC .............. 604/247; 604/256; 604/533

(58) Field of Classification Search
USPC .................. 604/246–256, 533–537
See application file for complete search history.

(56) References Cited

U.S. PATENT DOCUMENTS

| | | | |
|---|---|---|---|
| 274,447 A | 3/1883 | Kennish | |
| 1,578,517 A | 3/1926 | Hein | |
| 1,923,501 A | 8/1933 | Perry | |
| 2,210,098 A | 8/1940 | Ravenscroft | |
| 2,289,677 A | 7/1942 | Perelson | |
| 2,577,780 A | 12/1951 | Lockhart | |
| 2,756,282 A | 7/1956 | Deane | |
| 2,756,740 A | 7/1956 | Deane | |
| 2,809,665 A | 10/1957 | Crowe | |
| 2,847,995 A | 8/1958 | Adams | |
| 2,999,499 A | 9/1961 | Willet | |
| 3,134,380 A | 5/1964 | Armao | |
| 3,135,261 A | 6/1964 | Carroll | |
| 3,171,412 A | 3/1965 | Braun | |
| 3,176,021 A | 3/1965 | Volungis et al. | |
| 3,191,655 A | 6/1965 | McCord | |

(Continued)

FOREIGN PATENT DOCUMENTS

| | | |
|---|---|---|
| CA | 1 105 959 | 7/1981 |
| CA | 2 149 725 | 11/1995 |

(Continued)

OTHER PUBLICATIONS

U.S. Appl. No. 08/767,587, filed Dec. 16, 1996, including its prosecution history, Lopez et al.

(Continued)

*Primary Examiner* — Kami A Bosworth
*Assistant Examiner* — Imani Hayman
(74) *Attorney, Agent, or Firm* — Knobbe Martens Olson & Bear LLP

(57) ABSTRACT

A medical connector for use in a fluid pathway includes a substantially transparent housing having a proximal end with a proximal opening and a distal end with a distal opening, and a cavity extending therebetween. The connector provides a substantially visible fluid flow path extending through a substantial portion of the connector.

7 Claims, 21 Drawing Sheets

(56) References Cited

U.S. PATENT DOCUMENTS

| | | |
|---|---|---|
| 3,193,154 A | 7/1965 | Bross et al. |
| 3,334,860 A | 8/1967 | Bolton, Jr. |
| 3,352,531 A | 11/1967 | Kilmarx |
| 3,354,881 A | 11/1967 | Bloch |
| 3,385,301 A | 5/1968 | Harautuneian |
| 3,502,097 A | 3/1970 | Muller |
| 3,534,771 A | 10/1970 | Eyerdam et al. |
| 3,570,484 A | 3/1971 | Steer et al. |
| 3,630,199 A | 12/1971 | Gangarosa |
| 3,648,684 A | 3/1972 | Barnwell et al. |
| 3,659,602 A | 5/1972 | Cloyd |
| 3,717,174 A | 2/1973 | Dewall |
| 3,726,282 A | 4/1973 | Patel |
| 3,788,519 A | 1/1974 | Mengel |
| 3,830,241 A | 8/1974 | Dye et al. |
| 3,831,629 A | 8/1974 | Mackal et al. |
| 3,852,385 A | 12/1974 | Huggins |
| 3,861,388 A | 1/1975 | Vaughn |
| 3,889,675 A | 6/1975 | Stewart |
| 3,896,853 A | 7/1975 | Bernhard |
| 3,965,910 A | 6/1976 | Fischer |
| 3,974,832 A | 8/1976 | Kruck |
| 3,976,063 A | 8/1976 | Henneman et al. |
| 3,976,073 A | 8/1976 | Quick et al. |
| 3,977,403 A | 8/1976 | Patel |
| 3,986,508 A | 10/1976 | Barrington |
| 3,993,063 A | 11/1976 | Larrabee |
| 3,994,293 A | 11/1976 | Ferro |
| 4,005,710 A | 2/1977 | Zeddies et al. |
| 4,019,512 A | 4/1977 | Tenczar |
| 4,022,205 A | 5/1977 | Tenczar |
| 4,040,420 A | 8/1977 | Speer |
| 4,076,285 A | 2/1978 | Martinez |
| 4,079,738 A | 3/1978 | Dunn et al. |
| 4,080,965 A | 3/1978 | Phillips |
| 4,121,585 A | 10/1978 | Becker, Jr. |
| 4,128,098 A | 12/1978 | Bloom et al. |
| 4,133,441 A | 1/1979 | Mittleman et al. |
| 4,143,853 A | 3/1979 | Abramson |
| 4,149,535 A | 4/1979 | Volder |
| 4,161,949 A | 7/1979 | Thanawalla |
| 4,186,775 A | 2/1980 | Muroi |
| 4,187,846 A | 2/1980 | Lolachi et al. |
| 4,191,183 A | 3/1980 | Mendelson |
| 4,198,983 A | 4/1980 | Becker et al. |
| 4,200,096 A | 4/1980 | Charvin |
| 4,214,779 A | 7/1980 | Losell |
| 4,219,912 A | 9/1980 | Adams |
| 4,243,034 A | 1/1981 | Brandt |
| 4,257,416 A | 3/1981 | Prager |
| D259,278 S | 5/1981 | McCaw et al. |
| 4,294,249 A | 10/1981 | Sheehan et al. |
| 4,294,250 A | 10/1981 | Dennehey |
| 4,296,949 A | 10/1981 | Muetterties et al. |
| 4,306,705 A | 12/1981 | Svensson |
| 4,324,239 A | 4/1982 | Gordon et al. |
| 4,328,802 A | 5/1982 | Curley et al. |
| 4,329,987 A | 5/1982 | Rogers et al. |
| 4,334,551 A | 6/1982 | Pfister |
| 4,338,933 A | 7/1982 | Bayard et al. |
| 4,342,315 A | 8/1982 | Jackson |
| 4,346,703 A | 8/1982 | Dennehey et al. |
| 4,362,156 A | 12/1982 | Feller et al. |
| 4,387,879 A | 6/1983 | Tauschinski |
| RE31,315 E | 7/1983 | Jenkins et al. |
| 4,392,851 A | 7/1983 | Elias |
| 4,405,163 A | 9/1983 | Voges et al. |
| 4,405,312 A | 9/1983 | Gross et al. |
| 4,411,662 A | 10/1983 | Pearson |
| 4,417,890 A | 11/1983 | Dennehey et al. |
| 4,421,296 A | 12/1983 | Stephens |
| 4,429,856 A | 2/1984 | Jackson |
| 4,432,759 A | 2/1984 | Gross et al. |
| 4,432,765 A | 2/1984 | Oscarsson |
| 4,439,188 A | 3/1984 | Dennehey et al. |
| 4,439,193 A | 3/1984 | Larkin |
| 4,449,693 A | 5/1984 | Gerea |
| 4,457,749 A | 7/1984 | Bellotti et al. |
| 4,483,368 A | 11/1984 | Panthafer |
| 4,508,367 A | 4/1985 | Oreopoulos et al. |
| 4,511,359 A | 4/1985 | Vaillancourt |
| 4,512,766 A | 4/1985 | Vaillancourt |
| 4,564,054 A | 1/1986 | Gustavsson |
| 4,592,356 A | 6/1986 | Gutierrez |
| 4,607,868 A | 8/1986 | Harvey et al. |
| 4,610,469 A | 9/1986 | Wolff-Mooij |
| 4,617,012 A | 10/1986 | Vaillancourt |
| 4,619,640 A | 10/1986 | Potolsky et al. |
| 4,623,068 A | 11/1986 | Brown et al. |
| 4,645,494 A | 2/1987 | Lee et al. |
| 4,666,429 A | 5/1987 | Stone |
| 4,673,400 A | 6/1987 | Martin |
| 4,676,228 A | 6/1987 | Krasner et al. |
| 4,683,916 A | 8/1987 | Raines |
| 4,706,487 A | 11/1987 | Bandou et al. |
| 4,710,168 A | 12/1987 | Schwab et al. |
| 4,725,267 A | 2/1988 | Vaillancourt |
| 4,730,635 A | 3/1988 | Linden |
| 4,752,292 A | 6/1988 | Lopez et al. |
| D296,592 S | 7/1988 | Wellenstam |
| 4,758,224 A | 7/1988 | Siposs |
| 4,759,756 A | 7/1988 | Forman et al. |
| 4,775,369 A | 10/1988 | Schwartz |
| 4,778,447 A | 10/1988 | Velde et al. |
| 4,778,453 A | 10/1988 | Lopez |
| 4,781,702 A | 11/1988 | Herrli |
| 4,804,015 A | 2/1989 | Albinsson |
| D300,177 S | 3/1989 | Bellotti et al. |
| 4,810,241 A | 3/1989 | Rogers et al. |
| 4,813,938 A | 3/1989 | Raulerson |
| 4,819,684 A | 4/1989 | Zaugg et al. |
| 4,832,214 A | 5/1989 | Schrader et al. |
| 4,834,664 A | 5/1989 | Lin |
| 4,834,716 A | 5/1989 | Ogle, II |
| D303,013 S | 8/1989 | Konopka |
| 4,874,377 A | 10/1989 | Newgard et al. |
| 4,878,897 A | 11/1989 | Katzin |
| 4,880,414 A | 11/1989 | Whipple |
| 4,889,527 A | 12/1989 | Herrli |
| 4,915,687 A | 4/1990 | Sivert |
| 4,917,668 A | 4/1990 | Haindl |
| 4,919,167 A | 4/1990 | Manska |
| 4,928,212 A | 5/1990 | Benavides |
| 4,934,657 A | 6/1990 | Dodson |
| 4,943,896 A | 7/1990 | Johnson |
| 4,946,445 A | 8/1990 | Lynn |
| 4,963,133 A | 10/1990 | Whipple |
| 4,964,855 A | 10/1990 | Todd et al. |
| 4,966,199 A | 10/1990 | Ruschke |
| 4,969,883 A | 11/1990 | Gilbert et al. |
| D314,050 S | 1/1991 | Sone |
| 4,985,399 A | 1/1991 | Matsuda et al. |
| 4,987,181 A | 1/1991 | Bichon et al. |
| 4,991,413 A | 2/1991 | Arnalda |
| 4,991,629 A | 2/1991 | Ernesto et al. |
| 4,998,713 A | 3/1991 | Vaillancourt |
| 4,998,927 A | 3/1991 | Vaillancourt |
| 5,006,114 A | 4/1991 | Rogers et al. |
| 5,009,490 A | 4/1991 | Kouno et al. |
| 5,018,532 A | 5/1991 | Ethridge, III |
| 5,024,657 A | 6/1991 | Needham et al. |
| 5,031,675 A | 7/1991 | Lindgren |
| 5,041,087 A | 8/1991 | Loo et al. |
| 5,046,456 A | 9/1991 | Heyman et al. |
| 5,049,128 A | 9/1991 | Duquette |
| D321,250 S | 10/1991 | Jepson et al. |
| D321,251 S | 10/1991 | Jepson et al. |
| 5,061,253 A | 10/1991 | Yoshida |
| 5,064,416 A | 11/1991 | Newgard |
| 5,065,783 A | 11/1991 | Ogle, II |
| 5,071,411 A | 12/1991 | Hillstead |
| 5,098,385 A | 3/1992 | Walsh |
| 5,098,405 A | 3/1992 | Peterson et al. |
| 5,098,406 A | 3/1992 | Sawyer |

(56) References Cited

U.S. PATENT DOCUMENTS

| | | |
|---|---|---|
| 5,100,394 A | 3/1992 | Dudar et al. |
| 5,108,380 A | 4/1992 | Heritze et al. |
| 5,114,408 A | 5/1992 | Fleischhaker et al. |
| 5,116,361 A | 5/1992 | Kim et al. |
| 5,122,123 A | 6/1992 | Vaillancourt |
| 5,125,915 A | 6/1992 | Berry et al. |
| 5,135,489 A | 8/1992 | Jepson et al. |
| 5,137,524 A | 8/1992 | Lynn et al. |
| 5,147,333 A | 9/1992 | Raines |
| 5,154,703 A | 10/1992 | Bonaldo |
| 5,158,554 A | 10/1992 | Jepson et al. |
| 5,163,922 A | 11/1992 | McElveen, Jr. et al. |
| 5,167,238 A | 12/1992 | Newman |
| 5,167,636 A | 12/1992 | Clement |
| 5,171,234 A | 12/1992 | Jepson et al. |
| 5,180,761 A | 1/1993 | Shiao |
| 5,188,620 A | 2/1993 | Jepson et al. |
| 5,190,067 A | 3/1993 | Paradis et al. |
| 5,199,947 A | 4/1993 | Lopez et al. |
| 5,201,717 A | 4/1993 | Wyatt et al. |
| 5,201,722 A | 4/1993 | Moorehead et al. |
| 5,203,775 A | 4/1993 | Frank et al. |
| 5,211,638 A | 5/1993 | Dudar et al. |
| 5,215,538 A | 6/1993 | Larkin |
| 5,221,271 A | 6/1993 | Nicholson et al. |
| 5,224,515 A | 7/1993 | Foster et al. |
| 5,242,393 A | 9/1993 | Brimhall et al. |
| 5,242,423 A | 9/1993 | Goodsir et al. |
| 5,242,425 A | 9/1993 | White et al. |
| 5,242,432 A | 9/1993 | DeFrank |
| 5,251,873 A | 10/1993 | Atkinson et al. |
| 5,253,842 A | 10/1993 | Huebscher et al. |
| 5,255,676 A | 10/1993 | Russo |
| 5,256,155 A | 10/1993 | Yerlikaya et al. |
| 5,267,966 A | 12/1993 | Paul |
| 5,269,771 A | 12/1993 | Thomas et al. |
| 5,273,533 A | 12/1993 | Bonaldo |
| 5,280,876 A | 1/1994 | Atkins |
| 5,284,475 A | 2/1994 | Mackal |
| 5,290,254 A | 3/1994 | Vaillancourt |
| 5,292,308 A | 3/1994 | Ryan |
| 5,293,902 A | 3/1994 | Lapierie |
| 5,295,657 A | 3/1994 | Atkinson |
| 5,295,658 A | 3/1994 | Atkinson et al. |
| 5,301,686 A | 4/1994 | Newman |
| 5,306,265 A | 4/1994 | Ragazzi |
| 5,312,083 A | 5/1994 | Ekman |
| 5,312,377 A | 5/1994 | Dalhon |
| 5,322,518 A | 6/1994 | Schneider |
| 5,324,270 A | 6/1994 | Kayon et al. |
| 5,336,192 A | 8/1994 | Palestrant |
| 5,342,316 A | 8/1994 | Wallace |
| 5,342,326 A | 8/1994 | Peppel et al. |
| 5,344,414 A | 9/1994 | Lopez et al. |
| 5,348,542 A | 9/1994 | Ellis |
| 5,353,837 A | 10/1994 | Faust |
| 5,356,396 A | 10/1994 | Wyatt et al. |
| 5,360,413 A | 11/1994 | Leason et al. |
| 5,380,306 A | 1/1995 | Brinon |
| 5,389,086 A | 2/1995 | Attermeier et al. |
| 5,395,348 A | 3/1995 | Ryan |
| 5,398,530 A | 3/1995 | Derman |
| 5,401,245 A | 3/1995 | Haining |
| 5,402,826 A | 4/1995 | Molnar et al. |
| 5,402,982 A | 4/1995 | Atkinson et al. |
| 5,407,437 A | 4/1995 | Heimreid |
| 5,409,471 A | 4/1995 | Atkinson et al. |
| 5,411,483 A | 5/1995 | Loomas et al. |
| 5,411,499 A | 5/1995 | Dudar et al. |
| 5,417,673 A | 5/1995 | Gordon |
| 5,439,451 A | 8/1995 | Collinson et al. |
| 5,439,452 A | 8/1995 | McCarty |
| 5,441,487 A | 8/1995 | Vedder |
| 5,442,941 A | 8/1995 | Kahonen et al. |
| 5,456,676 A | 10/1995 | Nelson et al. |
| 5,470,319 A | 11/1995 | Mayer |
| 5,474,544 A | 12/1995 | Lynn |
| 5,480,393 A | 1/1996 | Bommarito |
| 5,487,731 A | 1/1996 | Denton |
| 5,501,426 A | 3/1996 | Atkinson et al. |
| 5,501,526 A | 3/1996 | Asai et al. |
| 5,509,433 A | 4/1996 | Paradis |
| 5,514,116 A | 5/1996 | Vaillancourt et al. |
| 5,520,665 A | 5/1996 | Fleetwood |
| 5,522,804 A | 6/1996 | Lynn |
| 5,533,708 A | 7/1996 | Atkinson et al. |
| 5,533,996 A | 7/1996 | Murphey et al. |
| 5,535,771 A | 7/1996 | Purdy et al. |
| 5,535,785 A | 7/1996 | Werge et al. |
| 5,540,661 A | 7/1996 | Tomisaka et al. |
| 5,549,566 A | 8/1996 | Elias et al. |
| 5,549,577 A | 8/1996 | Siegel et al. |
| 5,549,651 A | 8/1996 | Lynn |
| 5,555,908 A | 9/1996 | Edwards et al. |
| 5,556,388 A | 9/1996 | Johlin, Jr. |
| 5,562,632 A | 10/1996 | Davila et al. |
| 5,569,235 A | 10/1996 | Ross et al. |
| 5,573,516 A | 11/1996 | Tyner |
| 5,577,706 A | 11/1996 | King |
| 5,578,059 A | 11/1996 | Patzer |
| 5,597,536 A | 1/1997 | Mayer |
| 5,603,706 A | 2/1997 | Wyatt et al. |
| 5,609,584 A | 3/1997 | Gettig et al. |
| 5,616,129 A | 4/1997 | Mayer |
| 5,616,130 A | 4/1997 | Mayer |
| 5,617,897 A | 4/1997 | Myers |
| 5,620,424 A | 4/1997 | Abramson |
| 5,620,434 A | 4/1997 | Brony |
| 5,624,414 A | 4/1997 | Boettger |
| 5,632,735 A | 5/1997 | Wyatt et al. |
| 5,639,810 A | 6/1997 | Smith, III et al. |
| 5,660,205 A | 8/1997 | Epstein |
| 5,669,891 A | 9/1997 | Vaillancourt |
| 5,674,206 A | 10/1997 | Allton et al. |
| 5,676,346 A | 10/1997 | Leinsing |
| 5,685,866 A | 11/1997 | Lopez |
| 5,690,612 A | 11/1997 | Lopez et al. |
| 5,690,865 A | 11/1997 | Kindt-Larsen et al. |
| 5,694,686 A | 12/1997 | Lopez |
| 5,695,466 A | 12/1997 | Lopez et al. |
| 5,699,821 A | 12/1997 | Paradis |
| 5,700,248 A | 12/1997 | Lopez |
| 5,728,751 A | 3/1998 | Patnaik |
| 5,730,418 A | 3/1998 | Feith et al. |
| 5,738,663 A | 4/1998 | Lopez |
| 5,749,861 A | 5/1998 | Guala et al. |
| 5,769,825 A | 6/1998 | Lynn |
| 5,775,671 A | 7/1998 | Cote, Sr. |
| 5,776,113 A | 7/1998 | Daugherty et al. |
| 5,782,816 A | 7/1998 | Werschmidt et al. |
| 5,788,215 A | 8/1998 | Ryan |
| 5,797,897 A | 8/1998 | Jepson et al. |
| 5,806,551 A | 9/1998 | Meloul et al. |
| 5,806,831 A | 9/1998 | Paradis |
| 5,807,348 A | 9/1998 | Zinger et al. |
| 5,817,069 A | 10/1998 | Arnett |
| 5,820,601 A | 10/1998 | Mayer |
| 5,833,213 A | 11/1998 | Ryan |
| 5,836,923 A | 11/1998 | Mayer |
| 5,839,715 A | 11/1998 | Leinsing |
| 5,843,046 A | 12/1998 | Motisi et al. |
| 5,846,233 A | 12/1998 | Lilley et al. |
| 5,865,807 A | 2/1999 | Blake, III |
| 5,873,862 A | 2/1999 | Lopez |
| 5,882,348 A | 3/1999 | Winterton et al. |
| 5,899,888 A | 5/1999 | Jepson et al. |
| 5,901,942 A | 5/1999 | Lopez |
| 5,911,710 A | 6/1999 | Barry et al. |
| 5,928,204 A | 7/1999 | Lopez |
| 5,935,620 A | 8/1999 | Baudin |
| 5,947,954 A | 9/1999 | Bonaldo |
| 5,954,313 A | 9/1999 | Ryan |
| 5,957,898 A | 9/1999 | Jepson et al. |
| 5,967,490 A | 10/1999 | Pike |

(56) References Cited

U.S. PATENT DOCUMENTS

| | | |
|---|---|---|
| 5,979,868 A | 11/1999 | Wu et al. |
| 6,009,902 A | 1/2000 | Troiani et al. |
| 6,019,748 A | 2/2000 | Lopez |
| 6,029,946 A | 2/2000 | Doyle |
| 6,036,171 A | 3/2000 | Weinheimer et al. |
| 6,039,302 A | 3/2000 | Cote, Sr. et al. |
| 6,048,335 A | 4/2000 | Mayer |
| 6,050,978 A | 4/2000 | Orr et al. |
| 6,063,062 A | 5/2000 | Paradis |
| 6,079,432 A | 6/2000 | Paradis |
| 6,089,541 A | 7/2000 | Weinheimer et al. |
| 6,113,068 A | 9/2000 | Ryan |
| 6,116,571 A | 9/2000 | Hettinger |
| 6,117,114 A | 9/2000 | Paradis |
| 6,132,403 A | 10/2000 | Lopez |
| 6,132,404 A | 10/2000 | Lopez |
| 6,142,446 A | 11/2000 | Leinsing |
| 6,152,900 A | 11/2000 | Mayer |
| 6,162,206 A | 12/2000 | Bindokas et al. |
| 6,162,251 A | 12/2000 | Kredovski |
| 6,170,800 B1 | 1/2001 | Meloul et al. |
| 6,171,287 B1 | 1/2001 | Lynn et al. |
| 6,177,037 B1 | 1/2001 | Mayer |
| 6,183,448 B1 | 2/2001 | Mayer |
| 6,189,859 B1 | 2/2001 | Rohrbough et al. |
| 6,206,861 B1 | 3/2001 | Mayer |
| 6,210,624 B1 | 4/2001 | Mayer |
| 6,213,996 B1 | 4/2001 | Jepson et al. |
| 6,228,065 B1 | 5/2001 | Lynn |
| 6,228,069 B1 | 5/2001 | Barth et al. |
| 6,245,048 B1 | 6/2001 | Fangrow et al. |
| 6,254,579 B1 | 7/2001 | Cogger et al. |
| 6,261,282 B1 | 7/2001 | Jepson et al. |
| 6,261,630 B1 | 7/2001 | Nazarova et al. |
| 6,279,783 B1 | 8/2001 | Brown et al. |
| 6,290,206 B1 | 9/2001 | Doyle |
| 6,299,131 B1 | 10/2001 | Ryan |
| 6,299,132 B1 | 10/2001 | Weinheimer |
| 6,325,782 B1 | 12/2001 | Lopez |
| 6,364,869 B1 | 4/2002 | Bonaldo |
| 6,428,520 B1 | 8/2002 | Lopez et al. |
| 6,444,324 B1 | 9/2002 | Yang et al. |
| 6,482,188 B1 | 11/2002 | Rogers et al. |
| D468,016 S | 12/2002 | Mosler et al. |
| 6,541,802 B2 | 4/2003 | Doyle |
| 6,543,745 B1 | 4/2003 | Enerson |
| 6,572,592 B1 | 6/2003 | Lopez |
| 6,585,229 B2 | 7/2003 | Cote, Sr. et al. |
| 6,595,964 B2 | 7/2003 | Finley et al. |
| 6,595,981 B2 | 7/2003 | Huet |
| 6,599,273 B1 | 7/2003 | Lopez |
| 6,605,076 B1 | 8/2003 | Jepson et al. |
| 6,609,696 B2 | 8/2003 | Enerson |
| 6,635,044 B2 | 10/2003 | Lopez |
| 6,651,956 B2 | 11/2003 | Miller |
| 6,656,517 B2 | 12/2003 | Michal et al. |
| 6,669,673 B2 | 12/2003 | Lopez |
| 6,669,681 B2 | 12/2003 | Jepson et al. |
| 6,673,053 B2 | 1/2004 | Wang et al. |
| 6,682,509 B2 | 1/2004 | Lopez |
| 6,689,109 B2 | 2/2004 | Lynn |
| 6,695,817 B1 | 2/2004 | Fangrow |
| 6,706,022 B1 | 3/2004 | Leinsing et al. |
| 6,712,791 B2 | 3/2004 | Lui et al. |
| 6,727,294 B2 | 4/2004 | Kanayama et al. |
| 6,740,063 B2 | 5/2004 | Lynn |
| 6,745,998 B2 | 6/2004 | Doyle |
| 6,755,391 B2 | 6/2004 | Newton et al. |
| 6,758,833 B2 | 7/2004 | Lopez |
| 6,783,709 B2 | 8/2004 | Harreld et al. |
| 6,802,490 B2 | 10/2004 | Leinsing |
| 6,808,161 B1 | 10/2004 | Hishikawa |
| 6,840,501 B2 | 1/2005 | Doyle |
| 6,848,139 B2 | 2/2005 | Simon et al. |
| 6,866,656 B2 | 3/2005 | Tingey et al. |
| 6,869,426 B2 | 3/2005 | Ganem |
| 6,871,838 B2 | 3/2005 | Raines et al. |
| 6,883,778 B1 | 4/2005 | Newton et al. |
| 6,892,998 B2 | 5/2005 | Newton |
| 6,908,459 B2 | 6/2005 | Harding et al. |
| 6,916,309 B2 | 7/2005 | Fangrow, Jr. |
| 6,932,795 B2 | 8/2005 | Lopez et al. |
| 6,964,406 B2 | 11/2005 | Doyle |
| 6,991,215 B2 | 1/2006 | Kiehne |
| 6,994,315 B2 | 2/2006 | Ryan et al. |
| 7,014,169 B2 | 3/2006 | Newton et al. |
| 7,025,744 B2 | 4/2006 | Utterberg et al. |
| 7,033,339 B1 | 4/2006 | Lynn |
| 7,037,302 B2 | 5/2006 | Vaillancourt et al. |
| 7,044,441 B2 | 5/2006 | Doyle |
| 7,074,216 B2 | 7/2006 | Fowles et al. |
| 7,100,890 B2 | 9/2006 | Cote et al. |
| 7,104,520 B2 | 9/2006 | Leinsing et al. |
| 7,114,701 B2 | 10/2006 | Peppel |
| 7,125,396 B2 | 10/2006 | Leinsing et al. |
| 7,140,592 B2 | 11/2006 | Phillips et al. |
| 7,184,825 B2 | 2/2007 | Leinsing et al. |
| 7,244,249 B2 | 7/2007 | Leinsing et al. |
| 7,252,652 B2 | 8/2007 | Moorehead et al. |
| 7,264,859 B2 | 9/2007 | Rouns et al. |
| 7,306,197 B2 | 12/2007 | Parrino et al. |
| 7,306,199 B2 | 12/2007 | Leinsing et al. |
| 7,314,061 B2 | 1/2008 | Peppel |
| 7,329,249 B2 | 2/2008 | Bonaldo |
| 7,335,182 B1 | 2/2008 | Hilaire |
| 7,357,792 B2 | 4/2008 | Newton et al. |
| 7,396,348 B2 | 7/2008 | Newton et al. |
| 7,422,369 B2 | 9/2008 | Bergman et al. |
| 7,470,261 B2 | 12/2008 | Lynn |
| 7,470,262 B2 | 12/2008 | Hiejima et al. |
| 7,497,848 B2 | 3/2009 | Leinsing et al. |
| 7,497,849 B2 | 3/2009 | Fangrow, Jr. |
| 7,510,545 B2 | 3/2009 | Peppel |
| 7,520,489 B2 | 4/2009 | Ruschke |
| 7,530,546 B2 | 5/2009 | Ryan et al. |
| 7,556,060 B2 | 7/2009 | Guala |
| 7,559,530 B2 | 7/2009 | Korogi et al. |
| 7,563,243 B2 | 7/2009 | Mendels |
| 7,581,561 B2 | 9/2009 | Funamara et al. |
| 7,584,767 B2 | 9/2009 | Funamura et al. |
| 7,588,563 B2 | 9/2009 | Guala |
| 7,591,449 B2 | 9/2009 | Raines et al. |
| 7,601,141 B2 | 10/2009 | Dikeman et al. |
| 7,615,035 B2 | 11/2009 | Peppel |
| 7,624,749 B2 | 12/2009 | Guala |
| 7,628,774 B2 | 12/2009 | Fangrow, Jr. |
| 7,645,274 B2 | 1/2010 | Whitley |
| 7,651,481 B2 | 1/2010 | Raybuck |
| 7,666,170 B2 | 2/2010 | Guala |
| 7,673,653 B2 | 3/2010 | Mijers et al. |
| 7,703,486 B2 | 4/2010 | Costanzo |
| 7,713,250 B2 | 5/2010 | Harding et al. |
| 7,717,882 B2 | 5/2010 | Harding |
| 7,717,886 B2 | 5/2010 | Lopez |
| 7,743,799 B2 | 6/2010 | Mosler et al. |
| 7,753,338 B2 | 7/2010 | Desecki |
| 7,753,892 B2 | 7/2010 | Newton et al. |
| 7,758,566 B2 | 7/2010 | Simpson et al. |
| 7,763,013 B2 | 7/2010 | Baldwin et al. |
| 7,763,199 B2 | 7/2010 | Fangrow |
| 7,771,383 B2 | 8/2010 | Truitt et al. |
| 7,784,766 B2 | 8/2010 | Guala |
| 7,815,168 B2 | 10/2010 | Vangsness et al. |
| 7,824,393 B2 | 11/2010 | Fangrow, Jr. |
| 7,837,658 B2 | 11/2010 | Cote, Sr. et al. |
| 7,841,581 B2 | 11/2010 | Thorne, Jr. et al. |
| 7,842,026 B2 | 11/2010 | Cahill et al. |
| 7,857,284 B2 | 12/2010 | Kimball et al. |
| 7,857,285 B2 | 12/2010 | Lee et al. |
| 7,857,802 B2 | 12/2010 | Brandenburger et al. |
| 7,857,805 B2 | 12/2010 | Raines |
| 7,862,537 B2 | 1/2011 | Zinger et al. |
| 7,867,204 B2 | 1/2011 | Bartholomew et al. |
| 7,879,012 B2 | 2/2011 | Kane et al. |

(56) References Cited

U.S. PATENT DOCUMENTS

| | | |
|---|---|---|
| 7,900,659 B2 | 3/2011 | Whitley et al. |
| 7,905,873 B2 | 3/2011 | Rondeau et al. |
| 7,909,056 B2 | 3/2011 | Truitt et al. |
| 7,914,502 B2 | 3/2011 | Newton et al. |
| 7,947,032 B2 | 5/2011 | Harding et al. |
| 7,954,515 B2 | 6/2011 | Gerst |
| 7,975,722 B2 | 7/2011 | Kiehne |
| 7,981,090 B2 | 7/2011 | Plishka et al. |
| 7,981,381 B2 | 7/2011 | Lurvey et al. |
| 7,984,730 B2 | 7/2011 | Ziv et al. |
| 7,988,128 B2 | 8/2011 | Wentling |
| 7,993,328 B2 | 8/2011 | Whitley |
| 7,998,134 B2 | 8/2011 | Fangrow |
| 8,006,953 B2 | 8/2011 | Bennett |
| D644,731 S | 9/2011 | Fangrow, Jr. |
| 8,015,990 B2 | 9/2011 | Pascal et al. |
| 8,021,354 B2 | 9/2011 | Huang |
| 8,034,021 B2 | 10/2011 | Mendels |
| 8,034,035 B2 | 10/2011 | Weaver et al. |
| 8,038,663 B2 | 10/2011 | Miner |
| 8,042,838 B2 | 10/2011 | Buckler et al. |
| 8,048,038 B2 | 11/2011 | Guala |
| 8,062,266 B2 | 11/2011 | McKinnon et al. |
| 8,062,267 B2 | 11/2011 | McKinnon et al. |
| 8,062,280 B2 | 11/2011 | Jepson et al. |
| 8,066,648 B1 | 11/2011 | Mark |
| 8,066,669 B2 | 11/2011 | Christensen et al. |
| 8,066,670 B2 | 11/2011 | Cluff et al. |
| 8,070,189 B2 | 12/2011 | Yow et al. |
| 8,070,725 B2 | 12/2011 | Christensen |
| 8,074,964 B2 | 12/2011 | Mansour et al. |
| 8,096,525 B2 | 1/2012 | Ryan |
| 8,100,868 B2 | 1/2012 | Newton et al. |
| 8,100,869 B2 | 1/2012 | Vangsness et al. |
| 8,105,314 B2 | 1/2012 | Fangrow |
| 8,123,738 B2 | 2/2012 | Vaillancourt |
| 8,133,209 B2 | 3/2012 | Guala |
| 8,136,330 B2 | 3/2012 | Ostler et al. |
| 8,137,303 B2 | 3/2012 | Stout et al. |
| 8,142,403 B2 | 3/2012 | Carlyon |
| 8,152,790 B2 | 4/2012 | Lopez et al. |
| 8,156,971 B2 | 4/2012 | Costanzo |
| 8,162,006 B2 | 4/2012 | Guala |
| 8,162,013 B2 | 4/2012 | Rosenquist et al. |
| 8,167,863 B2 | 5/2012 | Yow |
| 8,172,823 B2 | 5/2012 | Rondeau et al. |
| 8,177,760 B2 | 5/2012 | Rome et al. |
| 8,177,768 B2 | 5/2012 | Leinsing |
| 8,177,772 B2 | 5/2012 | Christensen et al. |
| 8,182,452 B2 | 5/2012 | Mansourt et al. |
| 8,197,452 B2 | 6/2012 | Harding et al. |
| 8,197,466 B2 | 6/2012 | Yokota et al. |
| 8,211,089 B2 | 7/2012 | Winsor et al. |
| 8,221,363 B2 | 7/2012 | Jepson |
| 8,221,391 B2 | 7/2012 | Fangrow, Jr. |
| 8,241,268 B2 | 8/2012 | Whitley |
| 8,277,424 B2 | 10/2012 | Pan |
| 8,286,657 B2 | 10/2012 | Belley et al. |
| 8,287,518 B2 | 10/2012 | Kitani et al. |
| 8,298,195 B2 | 10/2012 | Peppel |
| 8,298,196 B1 | 10/2012 | Mansour |
| 8,337,483 B2 | 12/2012 | Harding et al. |
| 8,361,408 B2 | 1/2013 | Lynn |
| 8,372,043 B2 | 2/2013 | Grimm et al. |
| 8,377,010 B2 | 2/2013 | Harding et al. |
| 8,382,741 B2 | 2/2013 | Chelak |
| 8,398,598 B2 | 3/2013 | Carlyon et al. |
| 8,398,607 B2 | 3/2013 | Fangrow, Jr. |
| 8,403,886 B2 | 3/2013 | Bialecki et al. |
| 8,403,894 B2 | 3/2013 | Lynn et al. |
| 8,403,905 B2 | 3/2013 | Yow |
| 8,408,226 B2 | 4/2013 | Raines et al. |
| 8,409,165 B2 | 4/2013 | Niedospial, Jr. et al. |
| 8,414,542 B2 | 4/2013 | Stroup |
| 8,439,880 B2 | 5/2013 | Rondeau |
| 8,444,628 B2 | 5/2013 | Fangrow, Jr. |
| 8,454,579 B2 | 6/2013 | Fangrow, Jr. |
| 8,529,524 B2 | 9/2013 | Newton et al. |
| 8,628,515 B2 | 1/2014 | Fangrow, Jr. et al. |
| 2001/0049508 A1 | 12/2001 | Fangrow, Jr. |
| 2002/0120333 A1 | 8/2002 | Keogh et al. |
| 2003/0199835 A1* | 10/2003 | Leinsing et al. .............. 604/256 |
| 2004/0006330 A1 | 1/2004 | Fangrow, Jr. |
| 2005/0020981 A1 | 1/2005 | Kurth |
| 2005/0059952 A1 | 3/2005 | Giuliano et al. |
| 2005/0121638 A1 | 6/2005 | Doyle |
| 2005/0222541 A1 | 10/2005 | Lopez et al. |
| 2006/0004331 A1 | 1/2006 | Fangrow, Jr. |
| 2006/0161115 A1 | 7/2006 | Fangrow, Jr. |
| 2006/0200088 A1 | 9/2006 | Lopez |
| 2006/0200089 A1 | 9/2006 | Lopez et al. |
| 2006/0200090 A1 | 9/2006 | Lopez et al. |
| 2006/0206061 A1 | 9/2006 | Lopez et al. |
| 2006/0211997 A1 | 9/2006 | Fangrow, Jr. |
| 2006/0211998 A1 | 9/2006 | Fangrow, Jr. |
| 2006/0211999 A1 | 9/2006 | Fangrow, Jr. |
| 2006/0212001 A1 | 9/2006 | Fangrow, Jr. |
| 2006/0212003 A1 | 9/2006 | Fangrow, Jr. |
| 2006/0212006 A1 | 9/2006 | Fangrow, Jr. |
| 2006/0224127 A1 | 10/2006 | Fangrow, Jr. |
| 2006/0264842 A1 | 11/2006 | Fangrow, Jr. |
| 2006/0264844 A1 | 11/2006 | Fangrow, Jr. |
| 2006/0264849 A1 | 11/2006 | Lopez et al. |
| 2006/0264909 A1 | 11/2006 | Fangrow, Jr. |
| 2006/0264910 A1 | 11/2006 | Fangrow, Jr. |
| 2006/0270999 A1 | 11/2006 | Fangrow, Jr. |
| 2006/0271016 A1 | 11/2006 | Fangrow, Jr. |
| 2006/0276757 A1 | 12/2006 | Fangrow, Jr. |
| 2006/0276758 A1 | 12/2006 | Fangrow, Jr. |
| 2007/0007478 A1* | 1/2007 | Leinsing et al. ........... 251/149.1 |
| 2007/0100284 A1 | 5/2007 | Leinsing et al. |
| 2007/0106205 A1 | 5/2007 | Connell et al. |
| 2007/0112312 A1 | 5/2007 | Fangrow, Jr. |
| 2007/0112313 A1 | 5/2007 | Fangrow, Jr. |
| 2007/0224865 A1 | 9/2007 | Fangrow, Jr. |
| 2007/0225425 A1 | 9/2007 | Nash et al. |
| 2007/0235676 A1 | 10/2007 | Vangsness et al. |
| 2007/0254000 A1 | 11/2007 | Guo et al. |
| 2007/0270756 A1 | 11/2007 | Peppel et al. |
| 2008/0039802 A1 | 2/2008 | Vangsness et al. |
| 2008/0086097 A1 | 4/2008 | Rasmussen et al. |
| 2008/0086099 A1 | 4/2008 | McKinnon et al. |
| 2008/0097407 A1 | 4/2008 | Plishka |
| 2008/0249508 A1 | 10/2008 | Lopez et al. |
| 2009/0005761 A1 | 1/2009 | Guala |
| 2009/0209922 A1 | 8/2009 | Boisjoly |
| 2009/0292252 A1 | 11/2009 | Lareau et al. |
| 2010/0011579 A1 | 1/2010 | Raines et al. |
| 2010/0030163 A1 | 2/2010 | Carrez et al. |
| 2010/0030164 A1 | 2/2010 | Kimball et al. |
| 2010/0036330 A1 | 2/2010 | Plishka et al. |
| 2010/0049157 A1 | 2/2010 | Fangrow |
| 2010/0059474 A1 | 3/2010 | Brandenburger et al. |
| 2010/0059702 A1 | 3/2010 | Mansour et al. |
| 2010/0063456 A1 | 3/2010 | Rahimy et al. |
| 2010/0063482 A1 | 3/2010 | Mansour |
| 2010/0108681 A1 | 5/2010 | Jepson et al. |
| 2010/0152680 A1 | 6/2010 | Memahon |
| 2010/0174242 A1 | 7/2010 | Anderson et al. |
| 2010/0241088 A1 | 9/2010 | Ranalletta et al. |
| 2010/0249723 A1 | 9/2010 | Fangrow, Jr. |
| 2010/0249724 A1 | 9/2010 | Cote, Sr. et al. |
| 2010/0249725 A1 | 9/2010 | Cote, Sr. et al. |
| 2010/0264343 A1 | 10/2010 | Jeory |
| 2010/0270792 A1 | 10/2010 | Lauer |
| 2010/0283238 A1 | 11/2010 | Deighan et al. |
| 2010/0292674 A1 | 11/2010 | Jepson et al. |
| 2010/0300556 A1 | 12/2010 | Carmody et al. |
| 2010/0324502 A1 | 12/2010 | Guala |
| 2011/0004183 A1 | 1/2011 | Carrez et al. |
| 2011/0015566 A1 | 1/2011 | Pan |
| 2011/0015580 A1 | 1/2011 | Stroup et al. |
| 2011/0022031 A1 | 1/2011 | Fangrow, Jr. |
| 2011/0024664 A1 | 2/2011 | Burnard et al. |

(56) References Cited

U.S. PATENT DOCUMENTS

| | | |
|---|---|---|
| 2011/0028914 A1 | 2/2011 | Mansour et al. |
| 2011/0028915 A1 | 2/2011 | Siopes et al. |
| 2011/0046572 A1 | 2/2011 | Fangrow |
| 2011/0048540 A1 | 3/2011 | Stroup |
| 2011/0054440 A1 | 3/2011 | Lewis |
| 2011/0060293 A1 | 3/2011 | Guala |
| 2011/0066119 A1 | 3/2011 | Cote, Sr. et al. |
| 2011/0087164 A1 | 4/2011 | Mosler et al. |
| 2011/0106046 A1 | 5/2011 | Hiranuma et al. |
| 2011/0125104 A1 | 5/2011 | Lynn |
| 2011/0130717 A1 | 6/2011 | David et al. |
| 2011/0130724 A1 | 6/2011 | Mansour et al. |
| 2011/0130726 A1 | 6/2011 | Crawford et al. |
| 2011/0130727 A1 | 6/2011 | Crawford et al. |
| 2011/0130728 A1 | 6/2011 | McKinnon |
| 2011/0152787 A1 | 6/2011 | Truitt et al. |
| 2011/0152832 A1 | 6/2011 | Foshee et al. |
| 2011/0166532 A1 | 7/2011 | Brandenburger et al. |
| 2011/0178493 A1 | 7/2011 | Okiyama |
| 2011/0230845 A1 | 9/2011 | Pascal et al. |
| 2011/0236258 A1 | 9/2011 | Lurvey et al. |
| 2011/0257590 A1 | 10/2011 | Winsor et al. |
| 2011/0257606 A1 | 10/2011 | Truitt et al. |
| 2011/0257607 A1 | 10/2011 | Whitley |
| 2011/0264037 A1 | 10/2011 | Foshee et al. |
| 2011/0266477 A1 | 11/2011 | Stroup |
| 2011/0275988 A1 | 11/2011 | Davis et al. |
| 2011/0276010 A1 | 11/2011 | Davis et al. |
| 2011/0276031 A1 | 11/2011 | Hoang et al. |
| 2011/0284561 A1 | 11/2011 | Rosenquist et al. |
| 2011/0295235 A1 | 12/2011 | Fangrow |
| 2011/0306940 A1 | 12/2011 | Miyasaka |
| 2011/0308651 A1 | 12/2011 | Ziv et al. |
| 2011/0319821 A1 | 12/2011 | Kitani et al. |
| 2011/0319859 A1 | 12/2011 | Zeytoonian et al. |
| 2012/0013121 A1 | 1/2012 | Weckstrom |
| 2012/0022469 A1 | 1/2012 | Alpert |
| 2012/0042971 A1 | 2/2012 | Py |
| 2012/0046636 A1 | 2/2012 | Kriheli |
| 2012/0046650 A1 | 2/2012 | Yow et al. |
| 2012/0053529 A1 | 3/2012 | Imai |
| 2012/0059312 A1 | 3/2012 | Dikeman et al. |
| 2012/0059314 A1 | 3/2012 | Eichhorst |
| 2012/0059334 A1 | 3/2012 | Pan |
| 2012/0059346 A1 | 3/2012 | Sheppard et al. |
| 2012/0065626 A1 | 3/2012 | Naftalovitz et al. |
| 2012/0095407 A1 | 4/2012 | Chebator et al. |
| 2012/0109077 A1 | 5/2012 | Ryan |
| 2012/0130305 A1 | 5/2012 | Bonnal et al. |
| 2012/0130352 A1 | 5/2012 | Naftalovitz et al. |
| 2012/0150129 A1 | 6/2012 | Jin et al. |
| 2012/0153201 A1 | 6/2012 | Larose et al. |
| 2012/0157928 A1 | 6/2012 | Mermet |
| 2012/0157933 A1 | 6/2012 | Newton et al. |
| 2012/0179108 A1 | 7/2012 | Delabie |
| 2012/0192968 A1 | 8/2012 | Bonnal et al. |
| 2012/0209238 A1 | 8/2012 | Rosenquist et al. |
| 2012/0215182 A1 | 8/2012 | Mansour et al. |
| 2012/0220977 A1 | 8/2012 | Yow |
| 2012/0220984 A1 | 8/2012 | Christensen et al. |
| 2012/0245564 A1 | 9/2012 | Tekeste et al. |
| 2012/0259292 A1 | 10/2012 | Koehler |
| 2012/0283702 A1 | 11/2012 | Fangrow, Jr. |
| 2012/0316514 A1 | 12/2012 | Mansour |
| 2012/0316536 A1 | 12/2012 | Carrez et al. |
| 2012/0323063 A1 | 12/2012 | Costanzo |
| 2012/0330277 A1 | 12/2012 | Winsor et al. |
| 2013/0012870 A1 | 1/2013 | Dikeman et al. |
| 2013/0030386 A1 | 1/2013 | Panian et al. |
| 2013/0035668 A1 | 2/2013 | Kitani et al. |
| 2013/0046315 A1 | 2/2013 | Woehr et al. |
| 2013/0053815 A1 | 2/2013 | Mucientes et al. |
| 2013/0060205 A1 | 3/2013 | Mansour et al. |
| 2013/0066293 A1 | 3/2013 | Garfield et al. |
| 2013/0138075 A1 | 5/2013 | Lambert |
| 2013/0226099 A1 | 8/2013 | Fangrow, Jr. |
| 2013/0253478 A1 | 9/2013 | Fangrow, Jr. |
| 2013/0289534 A1 | 10/2013 | Fangrow, Jr. |
| 2013/0331800 A1 | 12/2013 | Newton et al. |

FOREIGN PATENT DOCUMENTS

| | | |
|---|---|---|
| CA | 2 175 021 | 11/1996 |
| CH | 636526 | 6/1983 |
| CH | 670955 | 7/1989 |
| DE | 855 319 | 9/1952 |
| DE | 84 25 197.2 | 9/1985 |
| DE | 37 40 269 | 6/1989 |
| EP | 0 263 789 | 4/1988 |
| EP | 0 309 771 | 4/1989 |
| EP | 0 399 119 | 11/1990 |
| EP | 0 446 463 | 9/1991 |
| GB | 2 000 685 | 1/1979 |
| GB | 2 001 146 | 1/1979 |
| GB | 2 034 185 | 6/1980 |
| WO | WO 92/20736 | 11/1992 |
| WO | WO 99/59672 | 11/1999 |
| WO | WO 99/61093 | 12/1999 |
| WO | WO 03/018104 | 3/2003 |
| WO | WO 2005/115521 | 8/2005 |
| WO | WO 2006/013433 | 2/2006 |
| WO | WO 2006/062912 | 6/2006 |
| WO | WO 2008/048777 | 4/2008 |
| WO | WO 2009/052433 | 4/2009 |
| WO | WO 2009/111596 | 9/2009 |

OTHER PUBLICATIONS

U.S. Appl. No. 10/217,213, filed Dec. 16, 1996, including its prosecution history, Fangrow et al.
Capless Backcheck Valve, dated Sep. 3, 1993.
Caresite™ Luer Access Device, dated 2010.
F.D.A. 510(k) Summary of Safety and Effectiveness, dated Nov. 17, 1997.
Saechtling Tworzywa Sztuczne, WN-T Warszawa, 1999, V edition, pp. 224-225.
PASV Valve Connector Brochure, which appears to be at least as early as Feb. 20, 2001.
LifeShield TKO Anti-Reflux Device Brochure, appears to contain a date of Feb. 2008.
Nexus Medical Nexus TKO, appears to contain a date of Mar. 2006.
"Faulding Inc. receives FDA permission to market patented Safe-Connect Valve", dated Dec. 2, 1996.
MicroClave Connector Brochure. The MicroClave was available before Mar. 25, 2008.
MEDI-4955 Liquid Silicone Rubber from NuSil Silicone Technology, dated Dec. 17, 2010.
U.S. Appl. No. 14/137,732, filed Dec. 20, 2013, Fangrow.
BD Medical: Needleless IV Access Devices, one page, 2007.
CareFusion, Medegen Introduces MaxPlus® Clear, First and Only Clear Positive Displacement Connector for Use in Infusion Therapy, MaxGuard News, one page article, dated Mar. 10, 2008—Ontario, CA.
ClearLink, needleless IV access system, Baxter 2007 brochure in 2 pages.
Canadian Office Action, re CA Application No. 2,665,151, dated Dec. 17, 2013.
Japanese Notice of Reasons for Rejection, re JP Application No. 2012-502268, mailed Jan. 28, 2014.

* cited by examiner

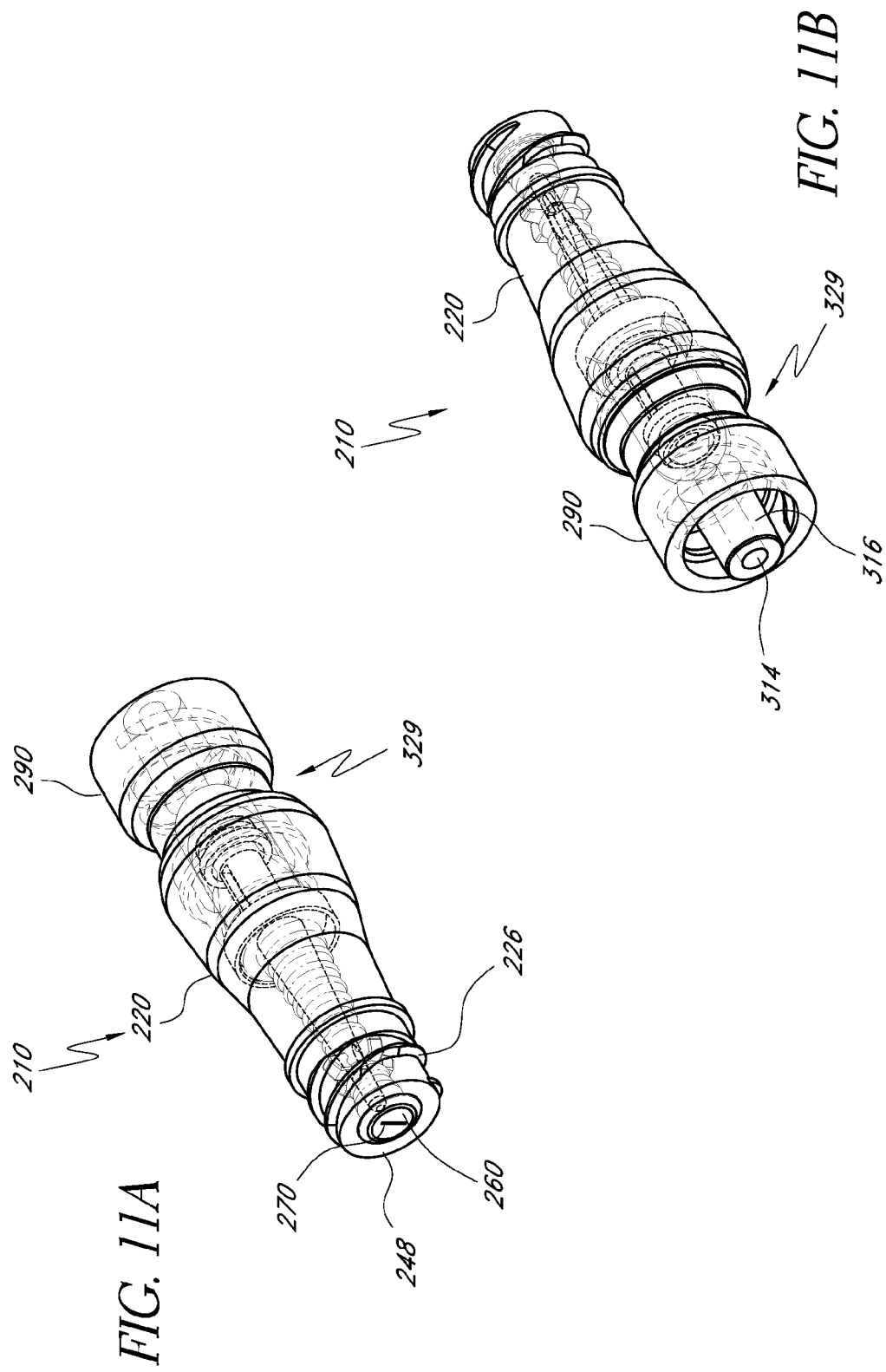

MEDICAL CONNECTORS AND METHODS OF USE

PRIORITY CLAIM AND INCORPORATION BY REFERENCE

The present application claims the benefit of U.S. Provisional Patent Application No. 61/345,554, filed May 17, 2010 (entitled "MEDICAL CONNECTOR WITH VISIBLE INTERNAL FLUID PATHWAY") and U.S. Provisional Patent Application No. 61/392,426, filed Oct. 12, 2010 (entitled "MEDICAL CONNECTORS AND METHODS OF USE"), the entire disclosures of which are hereby incorporated by reference.

This application also hereby incorporates by reference the entire disclosures of U.S. patent application Ser. No. 12/730,074 entitled "MEDICAL CONNECTORS AND METHODS OF USE", filed on Mar. 23, 2010, U.S. patent application Ser. No. 11/924,494 entitled "MEDICAL CONNECTOR", filed on Oct. 25, 2007, now published as US-2008-0103482-A1, published May 1, 2008, and U.S. patent application Ser. No. 11/381,526 entitled "MEDICAL VALVE AND METHOD OF USE", filed on May 3, 2006, now published as US-2006-0264892-A1, published Nov. 23, 2006.

BACKGROUND OF THE INVENTION

1. Field of the Invention

Embodiments of the invention relate generally to medical connectors through which fluids flow, and in particular, to self-sealing medical connectors.

2. Description of the Related Art

Closeable medical connectors or valves are useful in the administration of fluids in hospital and medical settings. They are often used to selectively open and close fluid pathways, and in particular for use in treating patients.

SUMMARY OF SOME EMBODIMENTS

Some embodiments disclosed herein relate to a closed, patient access system which can automatically reseal after administering fluid, medicaments, or other suitable substances (hereinafter, collectively referred to as "fluid") using a medical implement that connects or communicates with the system. A two-way valve can be employed, utilizing a reusable seal that may be repeatedly opened. The valve can facilitate the transfer of fluid, particularly liquid, while maintaining sterility. Before and after use, the valve can be swabbed in a conventional manner with a suitable substance to maintain sterility.

Some embodiments disclosed herein relate to a medical connector having transparent features that allow direct optical view of the fluid, or medicament, or bodily fluid, being transferred through the medical connector. In some embodiments, the connector includes a body member having a transparent wall with smooth inner and outer surfaces to provide a relatively distortion free optical view of the fluid level and fluid flow transferred through the connector. In some embodiments, the connector further includes a valve member and a base member having a support.

Some embodiments disclosed herein relate to a medical connector having a backflow resistance module configured to prevent fluid from being drawn into the connector when a backflow inducing event occurs (e.g., a syringe rebound, a syringe disconnection, etc.). In some embodiments, the backflow resistance module can include a variable volume chamber configured to change in volume in response to a backflow-inducing event and a check valve configured to resist backflow. In some embodiments, the medical connector can include a fluid diverter configured to direct fluid flowing through the medical connector into the variable volume chamber to prevent fluid stagnation therein. In some embodiments, the medical connector includes a body member, a base member, a seal member, a support member, and a valve member.

In accordance with another embodiment, a medical connector for use in a fluid pathway comprises a first portion having a first end and a second end, the first portion being substantially transparent, and a second portion having a first end and a second end, the first end of the second portion adjacent the second end of the first portion. The connector includes a first valve member having a first end and a second end, the first valve member disposed substantially within the first portion, wherein a substantially straight fluid flow path within the first portion and the second portion is visible through an external surface of the first portion and the second portion.

In accordance with another embodiment, a medical connector for use in a fluid pathway comprises a substantially transparent housing having a proximal end with a proximal opening and a distal end with a distal opening, and a cavity extending therebetween. The connector includes a substantially transparent valve member disposed substantially within the housing, and having a proximal end that substantially fills the housing proximal opening. The valve includes a proximal opening that is biased closed to obstruct fluid flow therethrough. The valve member is configured to selectively seal the housing proximal opening and to obstruct fluid communication between the housing proximal end and the housing distal end when the valve member is provided in a first position and to facilitate fluid communication between the housing proximal end and the housing distal end when the valve member is provided in a second position. The connector includes a support member configured to be substantially transparent and received within the valve member. The support includes an inner conduit that extends from adjacent a proximal tip portion having at least one opening that extends through the support member to the inner conduit to a distal end of the support member. The support member selectively facilitates fluid communication between the housing proximal end and the housing distal end. In some embodiments, the fluid communication between the housing proximal end and the housing distal end is established when the tip portion and at least a portion of the at least one opening protrude proximally through the valve proximal opening. A fluid flow path facilitates the fluid communication between the housing proximal end and the housing distal end and is visible through at least a portion of each of the transparent housing, the transparent valve member, and the transparent support member.

In accordance with another embodiment, a method of transferring fluid from a first medical implement to a second medical implement comprises providing a medical connector having a transparent housing with a proximal end and a proximal opening and a distal end and a distal opening. The connector includes a transparent flexible valve member disposed substantially within a cavity of the housing and with a valve member proximal end that substantially fills a portion of the cavity proximate the proximal opening. The valve includes an aperture adjacent the valve member proximal end. The connector further includes a transparent substantially hollow rigid support member configured to be received within the valve member and having an opening adjacent a proximal end of the support member. The flexible valve member is positionable between a first position that prevents fluid communication through the valve aperture and a second position that facilitates fluid communication through the valve aperture. The method includes coupling the housing proximal end to a first medical implement wherein a distal end of the first medical implement enters the housing proximal opening and may further include coupling the housing distal end to a second medical implement. The method further includes displacing the valve member by distally delivering the first medical implement within the housing and pushing a proximal end of the support member through the valve aperture, establishing fluid communication between the first medical implement and the second medical implement. As fluid flows between the first medical implement and the second medical implement, the fluid communication is optically visible through at least a portion of each of the transparent housing, the transparent valve member, and the transparent support.

In accordance with another embodiment, a medical connector comprises a housing configured to be substantially transparent and having a proximal opening adjacent a proximal end and a distal opening adjacent a distal end, and a fluid communication cavity extending therebetween. A first valve member can be disposed substantially within the housing and configured to be substantially transparent, and includes a proximal opening that is biased closed to obstruct fluid flow therethrough. The valve member is configured to obstruct fluid communication between the housing proximal end and the housing distal end when the valve member is provided in a first position and to facilitate fluid communication between the housing proximal end and the housing distal end when the valve member is provided in a second position. The connector includes a support member configured to be substantially transparent and to be received within the valve member, and having an inner conduit that extends from adjacent a proximal tip portion having at least one opening that extends through the support member to the inner conduit to a distal end of the support member. The support is configured to selectively facilitate fluid communication between the housing proximal end and the housing distal end, wherein the fluid communication between the housing proximal end and the housing distal end is established when the tip portion and at least a portion of the opening protrude through the valve proximal opening. The connector further includes a second valve member disposed substantially within the housing and configured to be substantially transparent, and having a proximal opening and a distal opening, and a wall member extending between the proximal opening and the distal opening. The wall deflects when a pressure differential between a proximal side of the second valve distal opening and a distal side of the second valve distal opening exceeds a predetermined threshold. A fluid flow path establishing the fluid communication between the housing proximal end and the housing distal end is visible through at least a portion of each of the transparent housing, the transparent valve member, and the transparent support member.

BRIEF DESCRIPTION OF THE DRAWINGS

Certain embodiments of the invention will now be discussed in detail with reference to the following figures. These figures are provided for illustrative purposes only, and embodiments of the invention are not limited to the subject matter illustrated in the figures.

FIG. 11A is a proximal perspective view of another embodiment of a valve or needleless connector.

FIG. 11B is a distal perspective view of the embodiment of the connector shown in FIG. 11A.

DETAILED DESCRIPTION OF THE PREFERRED EMBODIMENT

Figure 1:
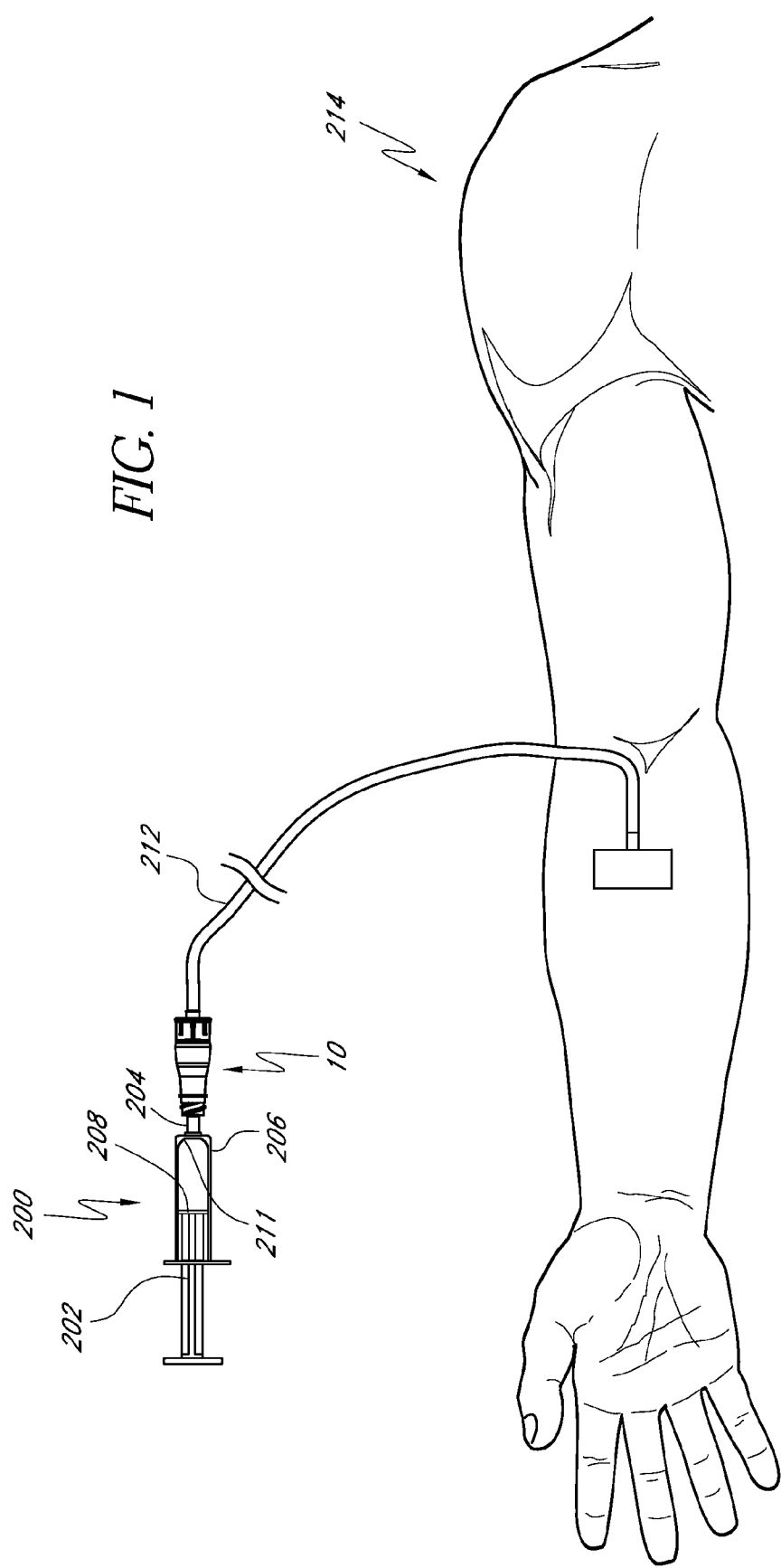
FIG. 1 is a schematic illustration showing an embodiment of a connector being used to inject fluids into the blood stream of a patient's arm.

The following detailed description is now directed to certain specific embodiments of the disclosure. In this description, reference is made to the drawings wherein like parts are designated with like numerals throughout the description and the drawings.

A variety of closing mechanisms are shown for closing one or more end portions of the needlefree connectors described herein. These closing mechanisms can function to substantially prevent and/or impede fluid from passing through the end portions of the connector when the closing mechanisms or valves are in a closed position. When the closing mechanisms are in an open position, such as when the connector is engaged with a needleless syringe or other medical connector, fluid can be permitted to pass through one or more end portions of the connectors. As used herein, terms such as "closed" or "sealed" and variants thereof should be understood to refer to obstructions or barriers to fluid flow. These terms should not be understood to require that a particular structure or configuration achieves a complete fluid closure in all circumstances.

In some aspects of the embodiments disclosed herein, a variety of structures and functions are shown and described for controlling and observing the fluid flow of medicaments or the like through medical connectors described herein. For example, it may be desirable to visually observe in real-time the fluid flow and/or the fluid position through the medical connector. Direct optical sight of the internal fluid can readily identify fluid leaks at sealing surfaces, contamination, residual fluids, blood, or the like, and minimize the risk of fouling the connector and thus requiring removal and replacement. As used herein, the terms "transparent" or "clear" and variants thereof should be understood to refer to the ability to substantially observe or see through a material or an object. These terms should not be understood to require that a particular structure or configuration achieves a completely undistorted view through the material or object in all circumstances.

In some aspects of the embodiments disclosed herein, a variety of structures are shown and described for controlling the flow of fluid and the passage of particles at a proximal inlet, or proximal opening, of a medical connector. A reusable medical connector requires repeated sterilization, for example, by conventional swabbing before inserting or after removing a medical implement to disinfect the silicone seal surface. Each swab sterilization procedure risks introducing contaminants to the internal portion, or cavity, of the medical connector to create a non-sterile condition, potentially inhibiting the purpose of the intended sterilization of the connector.

In some aspects of embodiments disclosed herein, a variety of structures are shown and described for controlling the flow of fluid inside a connector. These fluid control valves or mechanisms can facilitate the control of potentially undesirable fluid movement out of or into the connector. For example, it may be desirable to prevent, inhibit, or diminish negative flow or fluid ingress into the connector. As used herein, negative flow, retrograde flow, backflow, ingress flow, and related terms are used in accordance with their customary meanings in the medical connector field. In some cases, these terms refer to the flow of fluid into the connector due to an increase or effective increase in the internal volume of the fluid space within the connector, or due to an external draw or removal of fluid (such as by withdrawal of a portion of a medical implement, e.g. a syringe, or the like, previously inserted into the connector), or due to an external source of fluid pressure in a general retrograde direction, such as that caused by a patient's cough, or by an increase in a patient's blood pressure, or by disturbances in a fluid source (e.g., fluid volume in an IV bag diminishing or "running dry"), etc. Negative flow generally occurs in a direction generally opposite from or opposed to an intended flow of fluid into a patient.

One example of a source of negative flow occurs when a medical implement, such as a syringe, is removed from the proximal end, also referred to herein as the first or female end of the connector. As the syringe is removed, the fluid holding space inside the connector may increase. When that fluid space is in communication with a patient's fluid line catheter, the increase in fluid space inside the connector may draw fluid from the catheter into the connector from the distal end, also referred to herein as second or male end of the connector. This can be disadvantageous because negative flow can thereby draw blood from the patient into the opposite, or downstream, or patient, end of the catheter line. Such blood in the line can clot or otherwise foul the line, possibly requiring premature replacement and reinsertion of the catheter line, the connector, and/or other medical implements. Other sources of negative flow can be caused by a pump machine or a manual syringe due to springback of compressed rubber, or sealing, components of the pump or syringe that creates a void upon release of pressure that is capable of being filled with fluid from the catheter.

Some embodiments can generally provide optical clarity of the fluid flow within the internal cavities of a medical connector. Some embodiments can generally eliminate, diminish, minimize, or control the risk of contamination during sterilization of the connector ends. Some embodiments can generally eliminate, diminish, minimize, or control the effect of some or all sources of negative flow. Although the functionality of some of the embodiments disclosed herein is discussed in connection with a single source of negative flow (e.g., syringe rebound), it should be understood that many sources of negative flow can be eliminated, diminished, minimized, or controlled in similar or identical ways.

Figure 7:
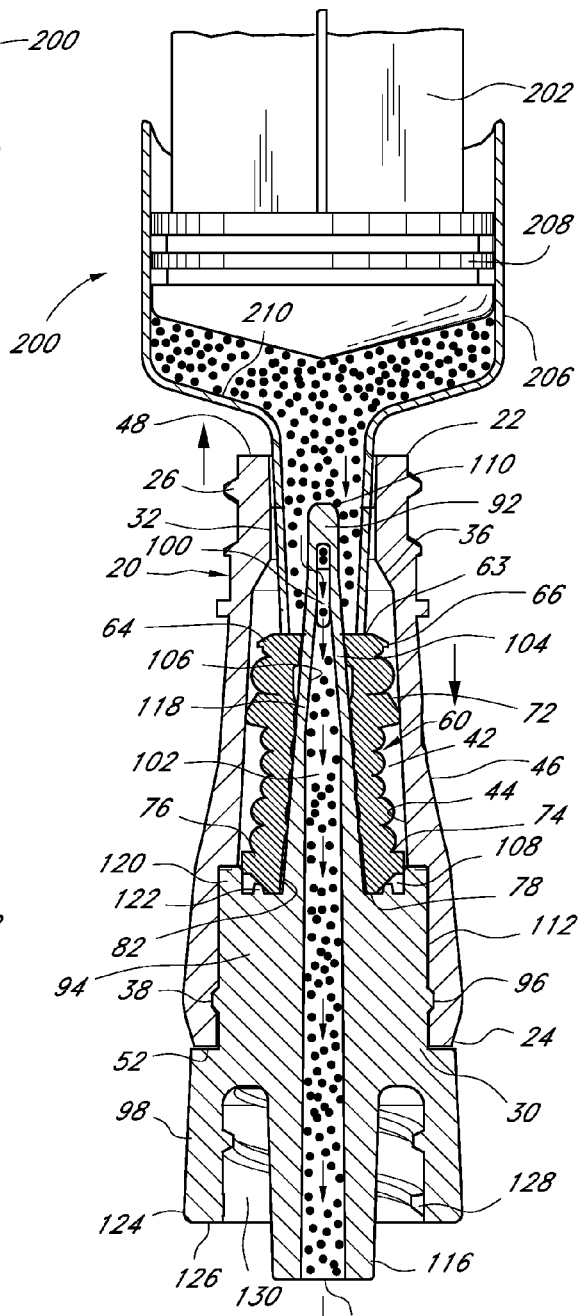
FIG. 7 is a section view of the embodiment of the connector shown in FIG. 2A, showing the seal member in a second or open position after the seal member has been contacted and opened by the syringe.

FIG. 1 is a schematic illustration showing an embodiment of a connector 10 being used to inject a fluid into the blood stream of a patient's arm. Embodiments of the connectors disclosed herein can generally also be used to withdraw fluid from the blood stream of a patient's arm. In other words, the connector 10 can be configured for a wide range of medical applications, and is not meant to be limited to the use illustrated in FIG. 1. As illustrated in FIG. 1, the connector 10 can be joined with a proximal end of a conduit 212 with the other, distal, end of the conduit 212 being in communication with a patient's 214 bloodstream. In this configuration, a syringe 200 can be inserted into the connector 10 so as to open a seal member 60, or a dynamic seal, of the connector 10. When the dynamic seal member 60 is in an open position, as illustrated in FIG. 7, the fluid from a syringe 200 can be transferred through the connector 10 and conduit 212 and into the patient's vasculature.

The syringe 200 illustrated in FIGS. 1 and 7-11 is an example of one type of medical implement that can be used with the connector 10. However, the connector 10 can be configured for use with a wide range of medical implements and is not limited to use with the example of the syringe 200 illustrated. The syringe 200 can be any suitable or common medical syringe used in the medical field. The connector 10 provides a convenient reusable and sterile connection device for a wide variety of medical implements that can be necessary to adequately treat the patient 214.

Figure 2:
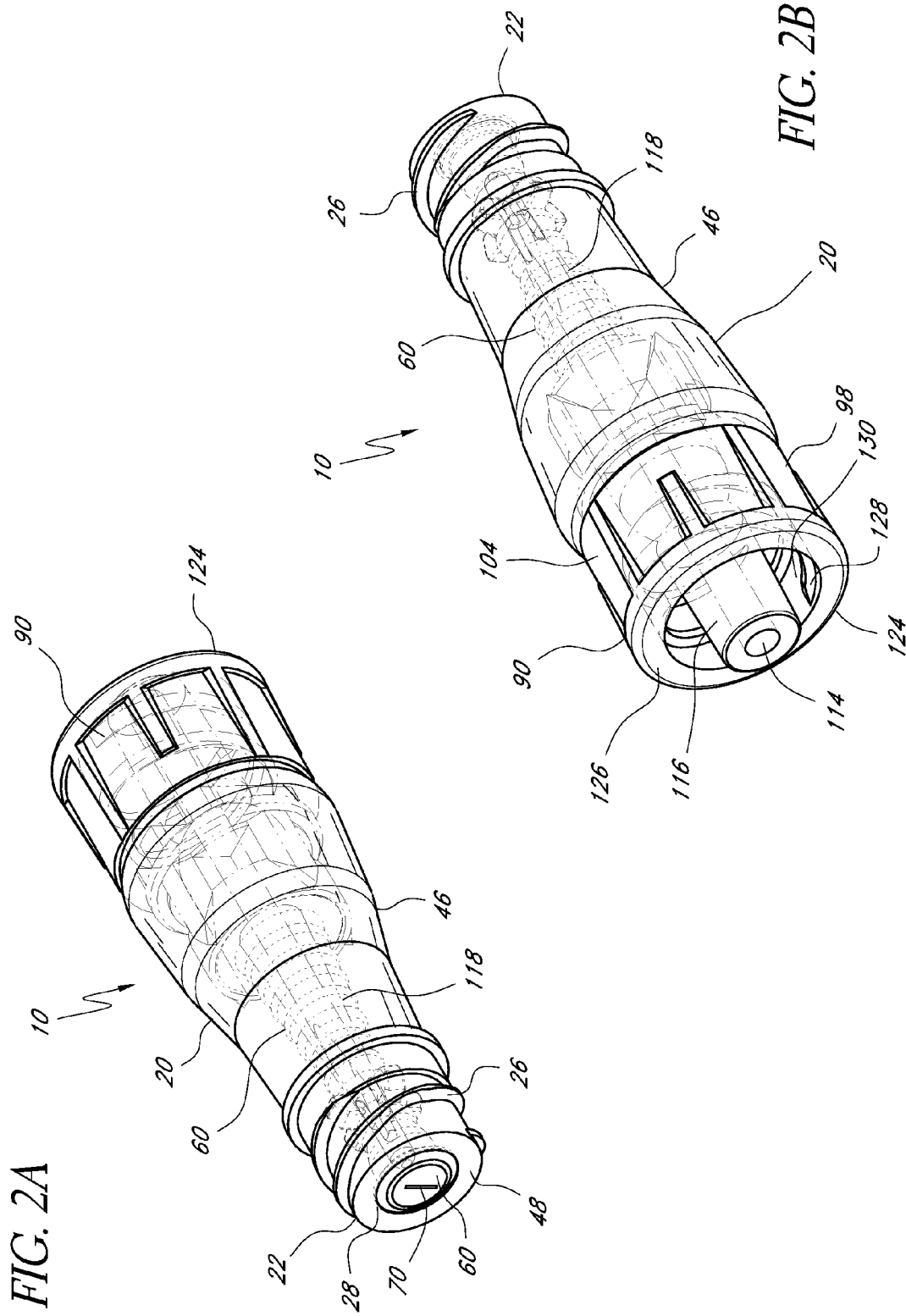
FIG. 2A is a proximal perspective view of an embodiment of a valve or needleless connector.
FIG. 2B is a distal perspective view of the embodiment of the connector shown in FIG. 2A.
Figure 3:
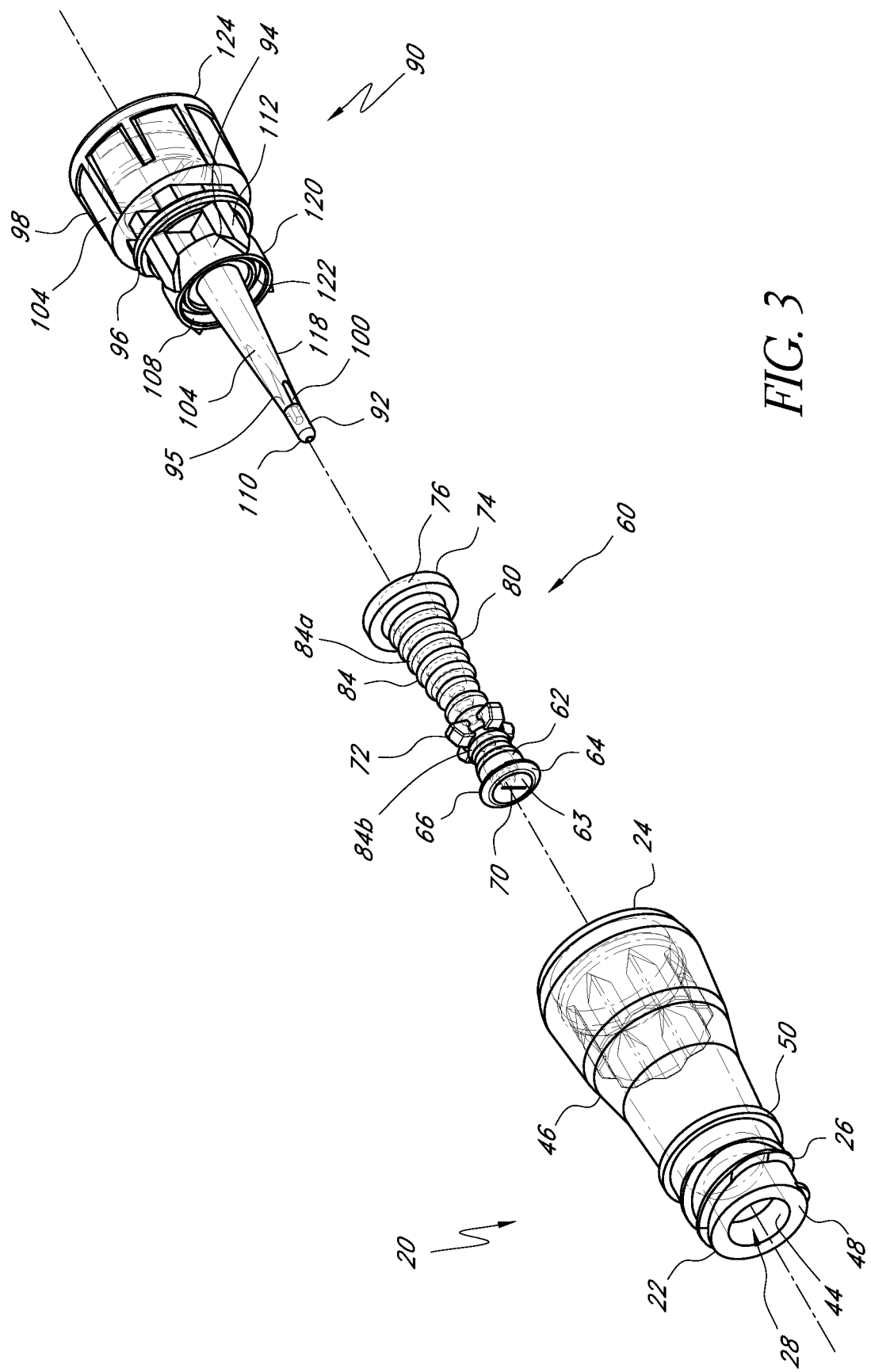
FIG. 3 is a proximal exploded view of the embodiment of the connector shown in FIG. 2A.
Figure 4:
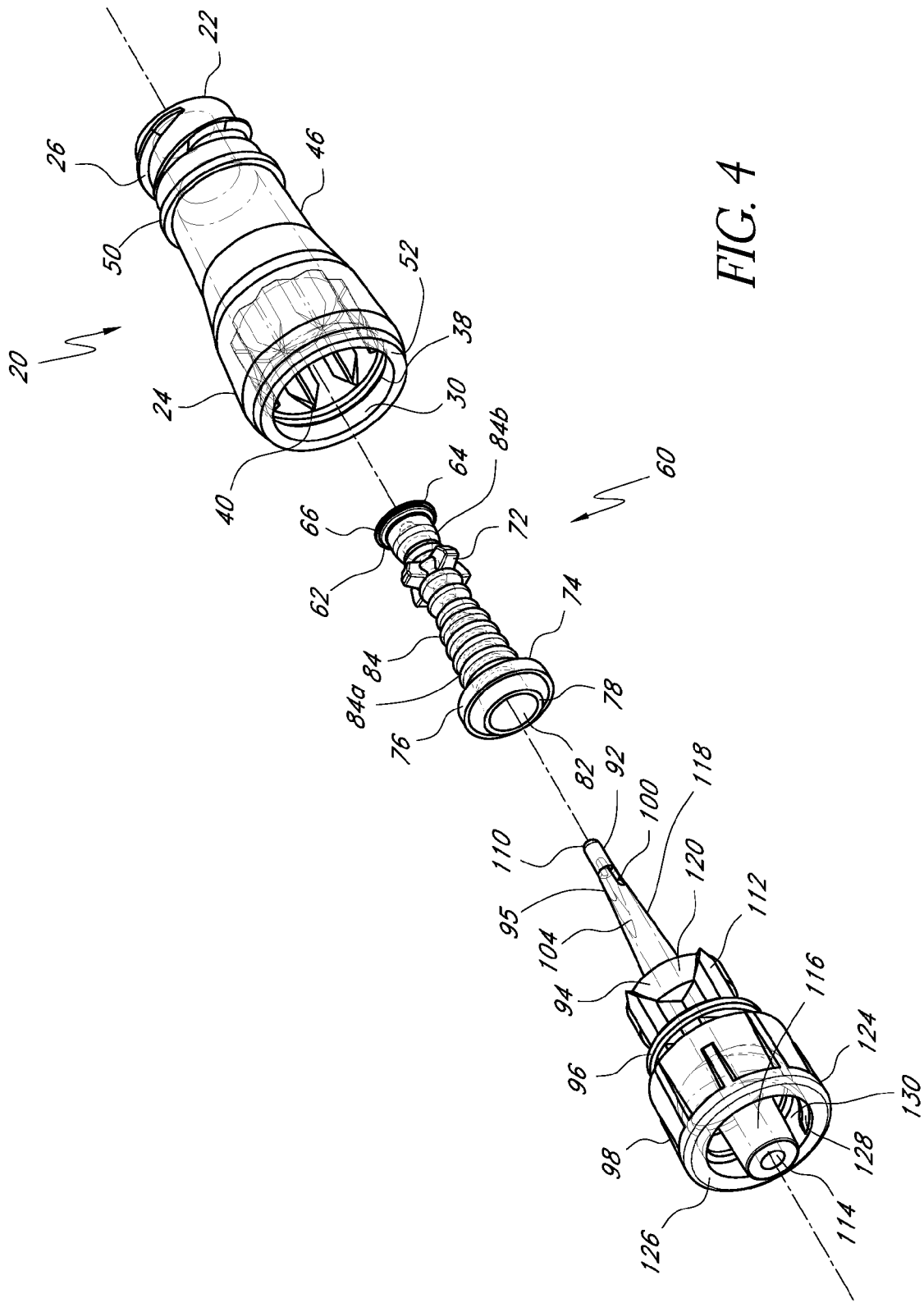
FIG. 4 is a distal exploded view of the embodiment of the connector shown in FIG. 2A.
Figure 5:
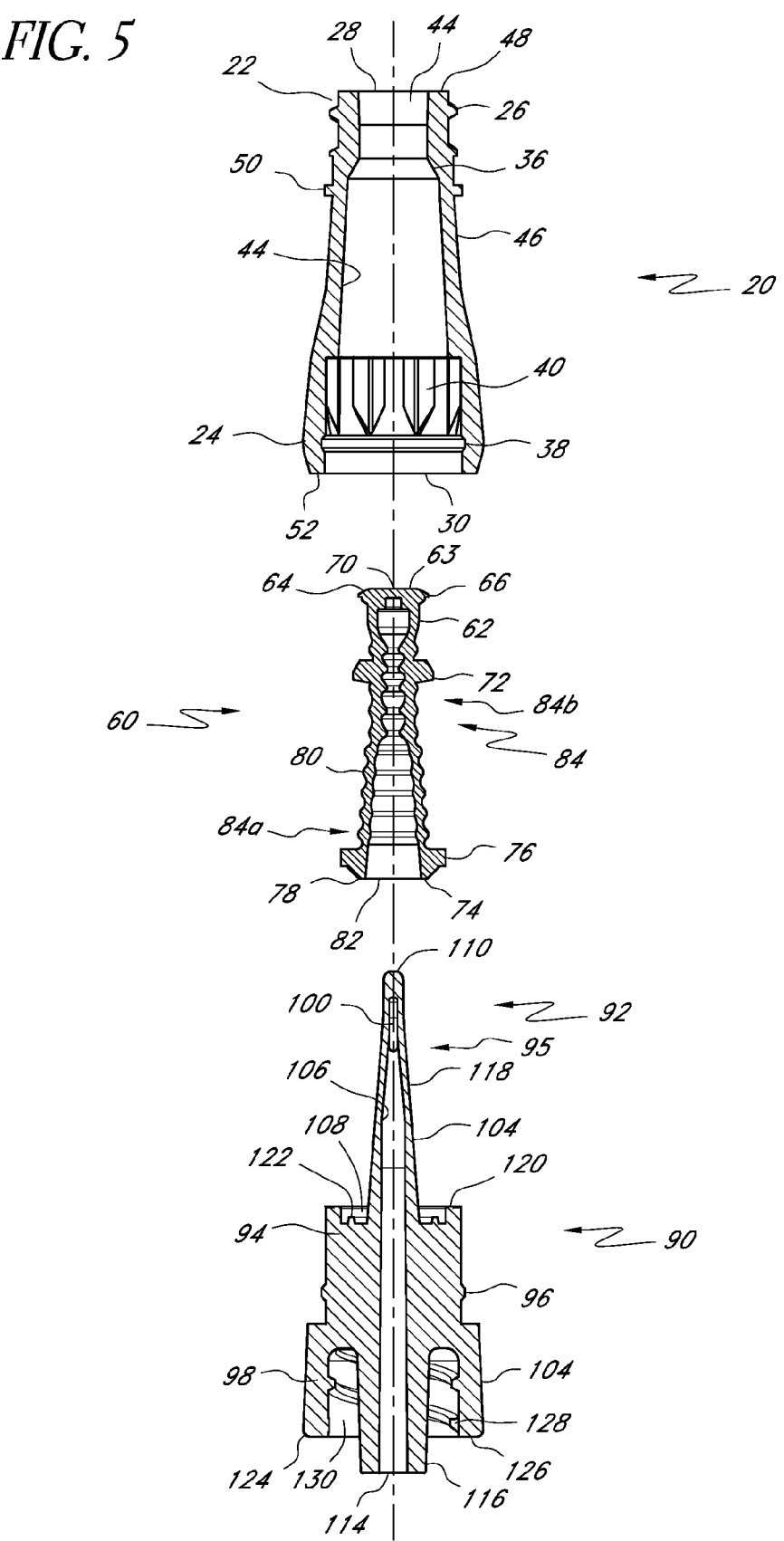
FIG. 5 is an exploded section view of the embodiment of the connector shown in FIG. 2A, taken through the axial centerline of the connector.

FIGS. 2A and 2B are perspective views of an embodiment of an assembly of a valve or needleless connector 10 that can be implemented to, for example, deliver medicaments to and/or extract bodily fluids from, a patient. FIGS. 3 and 4 are exploded views of the embodiment of the connector 10 shown in FIGS. 2A and 2B. FIG. 5 is an exploded cross-sectional view of the connector 10 shown in FIGS. 2A and 2B. With reference to FIGS. 2-5, some embodiments of the needleless connector 10 can include, inter alia, a body member 20, the seal member 60, a base member 90, and a support member 94 that can be a portion of the base member 90. The proximal portion of the body member 20, or first portion of the connector, can define a connector proximal end 22 and the distal portion of the base 90, or second portion of the connector, can define a connector distal end 124.

The term "proximal" is used herein to denote the end of the connector 10 at or near the body member 20 end of the connector. The term "distal" is used to denote the opposite end of the connector, e.g., the end of the connector 10 at or near the end of the base member 90. In the illustrated embodiment, the proximal end is configured as a female end and the distal end is configured as a male end. Any of the end portions, fittings, or other aspects of the connector 10 can be configured to accommodate any standard medical connector or implement, and can be configured to conform with ANSI (American National Standards Institute, Washington, D.C.) or other applicable standards. The term "medical implement" is used herein to denote any medical device commonly used in the medical field that can be connected or joined with any embodiments of the connectors disclosed herein. Examples of medical implements that are contemplated include, without limitation, tubing, luers, conduits, syringes, intravenous devices (both peripheral and central lines), closable male luer connectors (both integrally formed with a syringe or independent connectors), pumps, piggyback lines, and other components which can be used in connection with a medical valve or connector.

In the illustrated embodiment, the body member 20 and the base member 90 can be assembled together to form a housing that substantially encloses the seal member 60, or first valve member, and the support member 94. In one embodiment, the distal end of the body 20 can overlap the proximal end of the base 90. The support member 94 can include an elongate portion 118, or blunt cannula, or rigid support, which protrudes proximally and can be configured to receive the seal 60. The seal 60 can move axially, or longitudinally in a proximal to distal or distal to proximal direction about the elongate portion 118 within the housing formed by the body 20 and the base 90. The connector 10 can include a valve mechanism with a dynamic seal capability that is established between the engagement of the seal 60 and the elongate portion 118 that can have an open position and a closed position. The connector proximal end can receive a medical implement which can distally urge and compress the seal 60 about the elongate portion 118 to open the valve mechanism of the connector 10 and establish a fluid flow path through a radial opening 100 in the elongate portion 118. The fluid flow path can be directed from the medical implement into the elongate portion 118, through the base 20, and out an opening adjacent the distal end 124. The valve mechanism can be in a closed position when the seal 60 is extended over and covers, or encapsulates, the substantially full length of the elongate portion 118. The features of the body member 20, the seal member 60, the base member 90, the support member 94, the elongate portion 118, and the assembly therebetween are described in further detail below.

In some embodiments, the body member 20 can include a proximal end 22, or first end, and a distal end 24, or second end, with the body 20 extending therebetween. The body includes an outer surface 46 and an inner surface 44. The body can be transparent, or substantially transparent, such that objects or things positioned on the inside, or opposing side, of the body 20 are visible when viewed through the material of the body 20. The transparent body 20 facilitates viewing of the fluid medicament being delivered to, or bodily fluid being extracted from, the patient through the connector 10. In some embodiments, a substantially straight fluid flow path within the body 20 and the base 90 is visible through the external surface of the body and the base.

The proximal end 22 can have outwardly extending external threads 26 so that the connector 10 can be configured to couple, or be threadingly joined, to a male end of a standard luer connector or other suitable medical implements. In some embodiments, the outer surface 46 of the proximal end portion 22 can be smooth and generally cylindrical.

The body member 20 can have an annular ridge or protrusion 50 formed around an outside surface 46 of the body member 20 adjacent to the proximal end 22 of the body member 20. The protrusion 50 can be configured to engage a threaded collar or shroud (not shown) that may be included on a luer lock type syringe coupled onto the external threads 26, to prevent or inhibit over insertion of the syringe into the connector.

The body 20 can further include a proximal opening 28 disposed at the proximal end 22, and a distal opening 30 disposed at the distal end 24. In some embodiments, the proximal opening 28 is smaller than the distal opening 30. The body 20 can include a cavity 42, or passageway, in the internal portion of the body, and extending from the proximal end 22 to the distal end 24. The cavity 42 defines a passageway extending between the proximal opening 28 and the distal opening 30, such that an opening extends all the way through a longitudinal length of the body 20. The transparent body 20 material provides a clear optical view of the internal features of the body 20. For example, as illustrated in FIGS. 2A-B, the internal features of the seal member 60 and the support 94 can be viewed from outside of the body 20 through the outer surface 46.

In some embodiments, the cavity 42 is generally round, or cylindrical, and can include a plurality of different diameters at different longitudinal locations of the body 22. For example, in one embodiment, the proximal inner diameter of the body 20, or the cavity 42, can have a first diameter at the proximal end and transition at a predetermined longitudinal location to a second, larger diameter for the remaining longitudinal length of the body 20 to the distal end 24. In some embodiments, the inner diameter of the cavity 42 can have more than two diameters. In some embodiments, the inner diameter of the cavity 42 can be tapered for at least a portion of the longitudinal length. In some embodiments, the cavity 42 can include a plurality of different sized tapered portions, having different angled surfaces. In some embodiments, the cavity can have curved internal surfaces extending longitudinally. In some embodiments, the change in diameter can be smooth and blended to provide optical clarity through the transparent body wall. In some embodiments, the change in diameters can be abrupt and/or discontinuous with sharp or semi-sharp changes in surface geometry and provide transparent optical clarity of the internal features of the connector. In some embodiments, the cross-section geometry of the cavity 42, normal to the longitudinal axis, can have a shape other than circular or round, e.g. oval, polygonal, or the like, with corresponding changes in internal cross sectional areas along the longitudinal axis as described in detail above.

With continued reference to FIGS. 5-10, a proximal portion of the cavity 42 can establish a neck portion 32, or sealing surface, of the internal surface 44 of the body 20. The internal surface 44 can be substantially smooth for a portion of the first end, or proximal end, of the body 20 to facilitate the inner portion of the body 20 being visible through the external surface. The internal surface 44 can extend generally along the longitudinal direction of the connector 10 to facilitate the movement of the seal member 60 therein. The neck portion 32 is generally a tapered diameter along the longitudinal axis of the body 20 consistent with industry standards. In some embodiments, the mating sealing feature, a lip 66 of the seal 60, remains in contact with the cavity 42, or neck portion 32, internal surfaces.

The smooth internal surface 44 can provide an area, or a volume, for the seal member 60 to collapse into when the seal compresses longitudinally. The smooth surface area also provides a radially limiting contact surface for the seal member 60 when the seal moves, or expands, radially outward within the housing.

Figure 6:
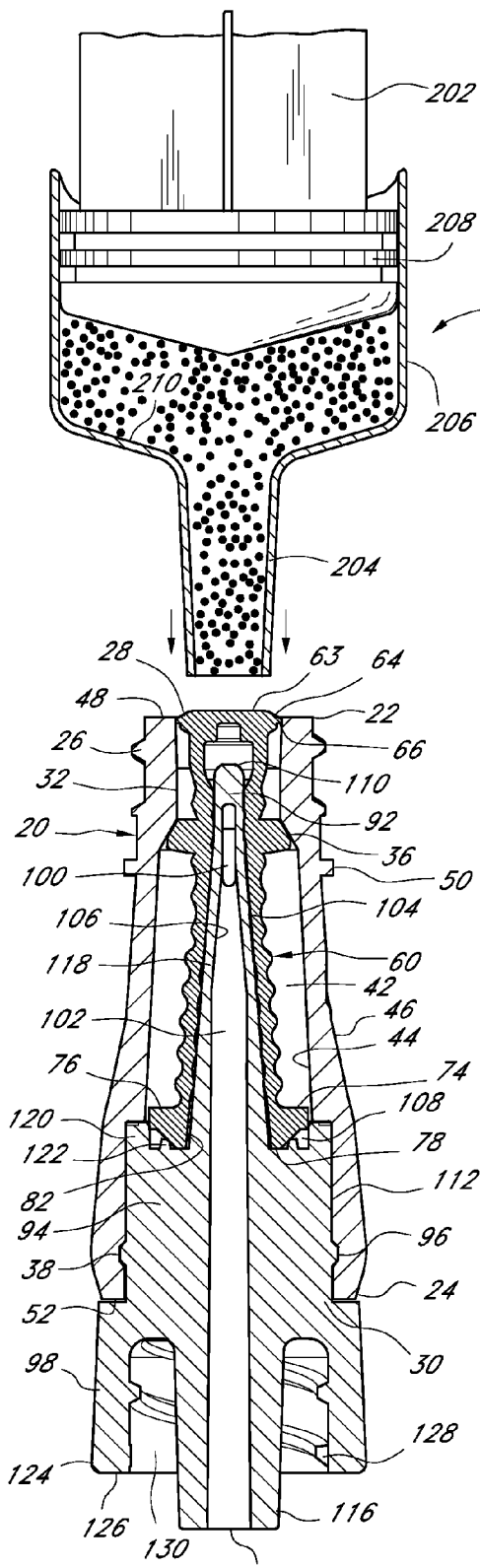
FIG. 6 is a section view of the embodiment of the connector shown in FIG. 2A, showing the seal member in a first or closed position before the seal member has been contacted and opened by a medical implement, such as the illustrated example of a syringe.

The proximal portion of the cavity 42 can include a radial projection 36, or a shoulder, or an inward transition, or an inward protrusion, which defines a change in the inner diameter of the body 20, or the cavity 42. The shoulder 36 defines the transition from a larger distal inner diameter to a smaller proximal inner diameter of the cavity 42. The transition of the shoulder can be angled, or tapered, relative to the longitudinal axis of the body 20. The shoulder 36 provides a physical stop, or retention means, for a portion of the seal member 60 in the connector 10 assembly, as illustrated in FIG. 6. The shoulder inward protrusion can transition from the body 20 larger diameter middle portion to the smaller neck portion 32 inner diameter. A suitable longitudinal position of the shoulder 36 can locate a proximal flange face 63 of the seal 60 on the same, or substantially same, plane as the body 20 proximal end face 48 to ease the swabability of the connector. The shoulder 36 can prevent the seal 60 from protruding beyond the body proximal end face 48, to provide a consistent positioning of the seal 60 relative to the end of the body 20.

In the illustrated embodiment of FIGS. 2-5, the body distal end 24 is shown with a plurality of channels 40 and an annular groove 38 disposed on the inner surface 44 of the cavity 42. The channels 40, or notches, extend longitudinally, or axially, about the distal portion 24 of the body 20. The plurality of channels 40 can be evenly spaced circumferentially about the inner surface 44 of the body 20. In some embodiments, the channels 40 can be spaced any suitable circumferential distance from one another. The channels 40 can be positioned proximally to the annular channel 38. The one or more channels 40, or notches, can be configured to receive the one or more protrusions 112 formed on the base member 90, which are described in greater detail below. The protrusions 112 and the notches 40 can be configured to join, or mate, or engage, one another to substantially prevent the body member 20 from rotating relative to the base member 90, thereby providing a more secure coupling, or joint, between the body member 20 and the base member 90.

The annular channel 38, or groove, extends around the inner surface 44 circumference of the cavity 42 adjacent the distal end 24, and can be positioned distal to the channels 40. The annular groove 38 can be configured to receive an annular protrusion 96 disposed about the base member 90 outer surface, which is described in greater detail below. The annular channel 38 lies substantially about a plane that is generally normal to the body 20 longitudinal axis. The annular channel 38 and the annular protrusion 96 can be configured to join, or mate, or engage, one another to provide a snap-fit type connection between the body member 20 and the base member 90. In this configuration, when the body member 20 has been joined with the base member 90 (as is illustrated in FIGS. 2A-B and 6-10), the annular channel 38 and the annular protrusion 96 substantially prevent the body member 20 from becoming disconnected from the base member 90. The base 90 and the body 20 are preferably transparent to provide a visual indicator of the integrity of the connector assembly. Many other structures and methods of attachment of these components can also be used, including the use of sonic welding or adhesives or the like.

In some embodiments, at least a portion of the longitudinal length of the hollow body 20 has a constant thickness wall. A constant wall thickness can provide a minimally distorted view of the interior cavity 42. In some embodiments, the body 20 can have a constant wall thickness for the full longitudinal length. In some embodiments, the various longitudinal portions include differing wall thicknesses with minimal effect on the optical clarity of the interior volume of the cavity 42.

The body member 20 and any other components or features of the connector 10 can be constructed from any of a number of suitable materials. For example, the body member 20 or any other suitable components or features of the connector 10 can be constructed from a relatively rigid transparent material, such as polycarbonate, glassed-filled GE Valox 420, polypropylene, other polymeric material, or the like, or any combination thereof. The body member 20, or any other suitable components or features of the connector 10, can also be constructed of a transparent hydrophobic material, such as Bayer Makrolon, or any other similar or suitable material. One or more components of the connector 10 or any other connector disclosed herein can include a suitable antimicrobial agent in any appropriate form, such as a component coating, as a part of the component matrix, or in any other suitable manner. In some embodiments, the antimicrobial agent may leach from or off one or more of the components during use or over time. In some embodiments, the antimicrobial agent can include a silver ion.

FIGS. 3-5 illustrate an embodiment of the seal member 60 in exploded perspective and cross-section views of the connector 10 shown in FIG. 2A-B. The pliable, or deformable, transparent seal 60 can include a proximal end 62, a distal end 78, and a seal body 84 extending therebetween. The proximal end 62 can include a proximal flange 64, the proximal face 63, the lip 66, and a slit 70. The distal end 78 can include a distal flange 74, an outer surface 76, and a distal opening 82. The seal 60 can further include a hollow interior, or passageway, or conduit, which extends axially, or longitudinally, from the slit 70 disposed in the enclosing proximal face 63 to the distal opening 82. The body 84 can further include a protrusion, or set of prongs, or collar 72 that is disposed about the outer diameter of the seal 60 and protrudes radially outward therefrom. The collar 72 can generally be positioned adjacent the seal proximal end 62. The seal 60 is generally transparent, and the internal conduit of the seal can be visible such that fluid and/or elongate portion 118 are substantially visible.

In some embodiments, as in the illustrated embodiment, the seal proximal end portion 62 can include the lip portion 66, or annular protrusion, which can have various geometric shapes formed thereon, e.g. rectangular, square, radiused, chamfered, or the like, or any combination thereof. The lip 66 can define the outermost radial portion of the seal proximal flange 64. The lip 66 can be a sealing feature of the proximal end 62, and can establish a sealing interface with the mating surface of the body neck 32.

With reference to FIGS. 2-6, the seal member 60 can be configured such that the seal proximal end portion 62, or first end, can be received by the opening 28, or the neck 32, disposed in the proximal end 22 of the body member 20. The annular lip 66 can be configured to contact the inside surface of the body 20 adjacent the opening 28, or the neck portion 32, to provide a seal therewith. The deformable seal 60 proximal end 62 can have an over-sized diameter, or any shape corresponding to the body 20 geometry, that is slightly larger than the inner diameter of the neck 32 and can establish an interference fit between the seal 60 and the body 20. The deformable seal 60 can be radially compressed to fit in the body 20 and can exert a radially outward sealing force that resists the radial inward compression. The seal proximal end 62 can fill the proximal opening 28 of the body 20 and seal, or isolate, the cavity 42 from the external environment, and promote a sterile connector internal volume. In some embodiments, the first valve member, or seal 60, can be disposed substantially within the first portion of the connector, or the body 20. The lip 66 can provide a seal therewith which generally resists the ingress of particulates or fluids into the connector, in particular any contaminants that might enter the connector during the repeated sterilization wipes of the seal face 63 and body end face 48. In some embodiments, the proximal end 22 of the body member 20 may include one or more grooves or recesses, not shown, configured to permit air or fluid to flow around the proximal end portion 62 of the seal member 60.

The seal proximal flange 64 can include the flat, or substantially flat, face 63 that encloses the proximal end 62 and can be generally perpendicular to the longitudinal axis of the seal. The slit 70, or seal first end opening, can be disposed in the proximal face 63. The proximal flange face 63 can establish the proximal most surface of the seal 60. The proximal flange face 63 can be positioned adjacent the proximal end 22 of the body 20 such that the seal flange face 63 and the body proximal flange 48 are substantially co-planar. In some embodiments, the face 63 can be any geometric shape, e.g. spherical, parabolic, or the like, or any combination thereof, rather than substantially flat.

The seal 60 proximal end 62 can include the collar 72, or prongs, that protrude radially outward from the outer surface of the seal. The collar 72 can extend around the full circumference of the seal 60, or a portion thereof, e.g. one, two, three, or four, or more, individual prong portions of a collar spaced about the circumference of the seal 60, for example, equally spaced around the circumference, or the like. Controlling the number of projections forming the collar 72 allows manipulation of the force required to open the connector. The gaps, or areas of thinner thickness, facilitate movement of the seal 60 along the elongate member 118 as the thicker projections resist expansion around the elongate member 118.

The collar 72 outer diameter can generally be smaller than the internal diameter of the middle portion of the body 20, but generally larger than the internal diameter of the neck 32, proximal opening 28, and internal cavity 42 adjacent the proximal end 22 of the body 20. The collar 72 can be configured to engage the body shoulder 36 and limit the axial extension or movement of the seal proximal end flange face 63. The collar 72, seal 60, and body 20 can be configured to position the flange face 63 at a substantially coplanar position relative the body proximal end face 48. The seal 60 and the body 20 can be configured to consistently and repeatedly align the seal proximal face 63 with the body end face 48 when the seal 60 returns to a biased extended length. The collar 72 distal surface can have a geometry that corresponds to the geometry of the shoulder 36, e.g. angled, radius, chamfered, or the like, or any combination thereof.

The distal end 78 of the seal member 60 can include an opening 82. In some embodiments, the opening 82 can be configured to receive the support member 94. In some embodiments, the distal end 78 further includes an outwardly extending flange 74 extending around or substantially around the seal member 60. The flange 74 can facilitate placement of the seal member 60 within the internal cavity of the body member 20 in some embodiments. In some embodiments, the seal distal flange 74 engages a support portion 94 disposed about the base 90.

The seal member 60 can be configured so that the slit 70, or first end opening, is biased to a closed position, so as to substantially prevent or inhibit liquid from flowing through the slit 70 formed in the seal member 60. Additionally, in some embodiments, as will be described in greater detail below, the slit 70 can be opened by delivering an elongate member, needle, protrusion, or the like, through the slit to separate the two biased side edges of the slit. In some embodiments, the slit 70 can be opened by distally compressing the seal member 60 proximal end 62 toward the seal distal end 78, wherein the seal proximal end 62 may slide over the elongate member 118 of the support member 94, causing at least a portion of the proximal end portion of the elongate member 118 to penetrate and pass through the slit 70. In some embodiments, the slit 70 can be configured to open without the support member 94 penetrating therethrough.

The seal member 60 can have a tapered resilient body portion 84 having a varied geometry, including bellows, convolutes, generally accordion-like, generally wave-like, generally alternating, or generally undulating contour shape configured to facilitate resilient compression and expansion of the seal member 60 as axial forces are applied to and removed from, respectively, the proximal end portion 62 of the seal member 60. In some embodiments, the body portion 84 can include a series of generally circular or o-ring shaped structures integrally formed together or separately formed and bonded together, or one or more groove structures oriented generally transverse to the axial direction of compression and expansion. These structures and contours can vary in diameter or cross-sectional shape and/or size. In some embodiments, the structures or contours can extend alternately generally inwardly and outwardly in a direction substantially perpendicular to the longitudinal axis of the seal member 60, as shown, for example, in FIGS. 3-6. The structure or contours can be formed in many configurations, such as in a helical configuration, or the like. In some embodiments, the geometry of the inner diameter will follow or coincide with the geometry of the outer diameter such that the thickness of the seal member wall can be substantially similar. In some embodiments, the geometry of the inner diameter is different than the geometry of the outer diameter such that the thickness of the seal member wall varies along the length of the seal member 60.

In some embodiments, the inside surface of the seal body 84 can approximately match the outside surface of the seal body 84 such that the inside surface of the seal body 84 can have the structure or contour described elsewhere herein. In some embodiments, the seal 60 convolutes 80 can have a substantially constant wall thickness. In some embodiments, the inside surface of the seal body 84 can generally extend radially inward when the corresponding portion of the outer surface of the seal body 84 extends radially outward, and the inside surface of the seal body 84 can generally extend radially outward when the corresponding portion of the outer surface extends radially inward. Thus, the seal body 84 can comprise a series of bulges, wherein the seal body 84 wall thickness alternates between thick and thin regions, as shown, for example, in FIG. 5. In some embodiments, the inside surface of the seal body 84 can generally extend radially inward when the corresponding portion of the outer surface of the seal body 84 extends radially inward, and the inside surface of the seal body 84 can generally extend radially outward when the corresponding portion of the outer surface extends radially outward. Thus, the seal body 84 can comprise a series of curved segments, wherein the wall of the seal body 84 has a more uniform thickness. In some embodiments, the inside surface of the seal body 84 can have a relatively smooth or flat surface contour.

The seal body 84 can have a generally consistent cross-sectional shape or size along the longitudinal length thereof, or the cross-sectional shape or size of the seal body 84 can vary along at least a portion of the longitudinal length thereof. In some embodiments, the shape of the inside of the seal body 84 can approximately match the outside surface of the elongate portion 118 of the support member 94. In some embodiments, the seal body 84 comprises a distal section 84a having a generally conical interior and exterior shape, and a proximal section 84b having a generally cylindrical interior and exterior shape. Many variations are possible, e.g. a cylindrical distal section and a conical proximal section, more than two sections having different geometric shapes, or the like.

The seal member 60 can be configured so that the seal body 84 is biased to an initial longitudinally, or axially, expanded first position, as illustrated in FIGS. 2-5. The convolute geometry of the seal 60 outer and/or inner surfaces can provide the spring-like bias of the expanded position. The convolutes allow seal 60 to longitudinally compress when the seal 60 is under longitudinally compressive loading. When an axial force is exerted on the seal member 60, the proximal end portion 62 and/or the seal body 84 can be caused to compress to a second position and, hence, axially retract so as to shorten the overall length of the seal member 60. When the axial force is removed from the seal member 60, the seal proximal end portion 62 and/or the seal body 84 can extend again as a result of the spring-like bias so as to return the seal member 60 to its initial or relaxed state. The bias of the convolutes can return the seal 60 to an unloaded, or at rest, expanded configuration when the compressive loading is removed. Although the seal member 60 can return to its relaxed state in a first or closed valve position, the seal member 60 can remain under some level of compression in the connector assembly, such as, for example, where the lip 66 of the proximal end portion 62 engages an inner surface or surfaces of the body member 20 under some degree of axial tension, or where the seal collar 72 engages the body shoulder 36.

The seal member 60, the proximal end portion 62 of the seal member 60, and the lip portion 66 can be integrally formed or can be separately formed and adhered or otherwise joined together using adhesive or any suitable material or method. In some embodiments, the seal member 60 or any other embodiment of a seal or seal member disclosed herein and any of the components or features thereof can be constructed from a number of different suitable materials, including silicone-based deformable materials, rubbers, or other suitable materials. Silicone-based deformable materials are among those that form fluid-tight closures with plastics and other rigid polymeric materials.

The seal member 60 or any other seal member disclosed herein can be formed from one, two, or more different materials. In some embodiments, different portions of the seal member 60 can be formed from different materials. For example, the seal member 60 can have a spring formed therein, not shown, to provide some or all of the restoring force desired to bias the seal member 60 to the closed position. The spring can be formed from a metal such as steel, plastic, or any other suitable rigid or pliable material, and can form the core of the seal member 60 such that the silicone rubber or other pliable sealing material encapsulates the spring. In some embodiments, the seal member 60 can be constructed just from a resilient or elastomeric material. Also by way of example, seal member 60 may include a resilient main body portion and a separately formed resilient proximal end portion. The separate pieces may be configured to engage each other, such as for example, by coupling to a guide member with a first end configured for attachment to the proximal end portion and a second end configured for attachment to the main body portion. The guide member may be manufactured from a more rigid material than used in either or both of the main body portion and the proximal end portion.

With continued reference to FIGS. 2-5, the base 90 and the support member 94 of an embodiment of the connector 10 is shown. The base 90 can be transparent and include a proximal portion 95 and a distal portion 124. The proximal portion 95 can include a tip portion 92, a tip 110, and the elongate portion 118, which can include at least one radial opening 100. The distal end 124 can include the support member 94, a shroud 98, an annular protrusion 96, protrusions 112, an opening 114, and a male protrusion tip 116.

FIG. 5 shows a cross-section view of an embodiment of the base 90 taken through the axial centerline of the base 90. With reference to FIGS. 2-5, in some embodiments, the base portion 90 can include the support member 94 having the elongate portion 118 projecting from the support 94 in the proximal direction, and a shroud 98 projecting from the support portion 94 in the distal direction. In some embodiments, one or more of these components of the illustrated base 90 can be omitted or replaced with a different component. For example, a base 90 need not include a support member 94 with an elongate portion 118.

In some embodiments, the one or more components of the illustrated base 90 and support member 94 can be separately formed and attached to one another via an adhesive, sonic welding, snap fit, or other suitable coupling manner, or any combination thereof. For example, the transparent elongate portion 118 and the transparent support portion 94 can be separately formed and attached by, for example, sonic welding. For example, the elongate portion 118 may be separately formed from the base member 90, and the elongate portion 118 and/or any other portion can be configured to move within the connector during use. For example, shroud 98 can be separately formed and later attached to base 90. In some embodiments, the entire base 90 can be integrally formed as a one-piece unit, to include the elongate portion 118, the support member 94, the shroud 98, and male protrusion tip 116.

In the illustrated embodiment, the at least one radial opening 100 is disposed adjacent the tip portion 92, or the proximal end 95, and can be in fluid communication with the conduit 102, or fluid passageway, extending generally axially, or longitudinally, through the base 90 to the distal opening 114. The conduit 102 can be defined by an inner surface 106 of the elongate portion 118. The radial opening can be a longitudinally oriented oval shape, or any other geometric shape in any other direction, e.g. round, rectangular, square, or the like. In some embodiments, the tip portion 92 can include two radial openings 100 disposed circumferentially substantially 180 degrees from one another. The fluid passageway 102 can extend through a substantial portion of the elongate portion 118, the support member 94, and the male tip protrusion 116. In some embodiments, the opening can be disposed at the proximal end of the tip 110.

As illustrated in FIGS. 2-5, the elongate portion 118 can have a tapered outer surface 104 and the proximal tip portion 92 can establish the proximal end of the elongate portion. The elongate portion can be configured to receive the seal 60 over, or onto, the outer surface 104 of the elongate portion 118. In some embodiments, the rigid support, or elongate portion 118 can be disposed substantially within the first portion of the connector, or the body 20. The outer surface 104 can be substantially smooth to provide for a slidable engagement with the inner surface of the seal 60 opening 82. In some embodiments, the outer surface 104 can include a roughened surface to provide selective friction for the sliding engagement between the outer surface 104 and the inner diameter surface of the seal 60 and/or may be used to prevent the formation of a vacuum therebetween. The roughened surface can be any form or shape coupled to, molded, formed, or machined into the outer surface 104, e.g. protruding knobs, full or portions of circumferential rings, random divots, scored surfaces, wavy surfaces, or the like, or any combination thereof.

The elongate portion 118 can include a lubricant applied to the outer surface 104 to facilitate the sliding, or slidable, engagement with the inner diameter surfaces of the seal 60. The lubricant can provide for an ease of sliding the seal proximal end 62 in a distal direction onto the expanding diameter of the tapered geometry of the elongate portion 118. The lubricant can include any suitable lubricant, e.g. silicone, or the like. In some embodiments, the roughened outer surface 104 can provide control, or resistance, to the lubricated sliding engagement between the outer surface 104 and inner diameter surface of the seal 60. The resistance, or control, can prevent excessive compression or too rapid of a compression or expansion of the seal member 60 during functional operation, or connection of a medical implement to the connector 10.

The proximal tip portion 92 can have a generally tapered, or generally conical, outer surface. In some embodiments, the tip portion 92 can be generally cylindrical. The elongate portion 118 can be configured so that the proximal tip portion 92 comprises a cross-sectional area that is significantly less than the cross-sectional area of the support portion 94. In some embodiments, the proximal tip portion 92 can be configured so that the proximal end portion 62 of the seal 60 can be distally retracted (e.g., repositioned from the expanded or initial position to the compressed position) relative to the proximal tip portion 92 of the support 94 without significant drag or resistance from the support member 94 or the elongate portion 118. In some embodiments, the proximal tip portion 92 has a sharp or rounded tip 110 configured to penetrate through the slit 70 formed in the seal 60 proximal flange face 63. In some embodiments, the tip 110 is integrally formed with the tip portion 92 and the rest of the elongate portion 118. In some embodiments, the proximal end of the elongate portion 118 includes a hole positioned at its proximal tip and the passageway 102 may extend from the opening 114 to the opening at the tip. In some such embodiments, it may be advantageous to include a seal 60 with an opening that is molded in the open position to facilitate passage of the seal 60 over the open tip 110.

In the assembled configuration, the seal 60 can be supported by the support 94 so that the elongate portion 118 is received within the opening 82 formed within the seal 60. The seal member 60 can thus be supported within the body member 20 and the base member 90. The body 20 and the base 90 can be joined together to provide the rigid housing that substantially encapsulates the seal 60 and the support 94 in the internal cavity 42.

With continued reference to FIGS. 2-5, additional features of the body member 20 and the base member 90 will now be described. The support portion 94 can have an outer annular wall 120 cooperating with the distal end of the base 90 to form an annular channel 108. The channel 108 can be configured to receive a portion of the seal distal end 78. The annular channel 108 can include a seal step 122 protruding proximally from the distal surface of the channel 108 that is configured to receive and engage the seal distal end 78. In some embodiments, the support portion 94 can be configured to secure the seal distal end 78 relative to the support 94 so as to prevent the seal distal end 78 from translating in a distal axial direction relative to the support portion 94. For example, the seal distal end 78 can be sandwiched, encompassed between portions of the base 90 and the body 20. In some embodiments, the channel 108 can be configured to secure the seal distal end 78 relative to the support portion 94 of the support member 94 so as to prevent the distal end portion 78 from translating in a radial direction relative to the support portion 94. The seal 60 can be assembled with the support 94 with or without adhering or otherwise fixing the seal distal end 78 to the support portion 94, e.g. mechanically sandwiched between a protruding portion of the body 20 and the support portion 94, or the like. Indeed, in some embodiments, the distal end of the seal member 60 can "float" in the internal cavity of the body member 20 and can translate axially, or longitudinally, as the seal member 60 moves from a closed position to an open position. In some embodiments, though not fixed to the support portion 94, the seal 60 may nevertheless remain relatively still relative to the support portion 94 because it may be under compression in both the open and closed positions.

The base 90 can have the male tip protrusion 116 projecting distally therefrom. The male tip protrusion 116 distal end can define an opening 114 through the male protrusion that can be in fluid communication with the cavity 42 formed inside the body 20 and base 90. In some embodiments, as illustrated, the male tip protrusion 116 can be substantially open to fluid communication in both the open and closed positions of the valve. Additionally, a shroud 98 may include radially outward protrusions or other features (not shown) thereon designed to enhance the grip of the connector 10 and internal threads 128 formed on an inside surface 130 of the shroud 98. The base member 90 can be configured to conform with ANSI standards for medical connectors.

As mentioned, the base 90, including the elongate member 118 and the support 94, can be formed from the same type of rigid materials as can be used to form the body member 20. In some embodiments, for example, the base member 90 can be formed from a semi-rigid or even more flexible material than used for the body member 20, or other components of the connector 10. In some embodiments, the base 90 (and any other embodiment of a base or support member of any other connector disclosed herein) can be formed integrally with the elongate member 118 and the support 94 (or any other embodiment of a base member of any other connector disclosed herein), or can be formed separately and thereafter joined with the support member or the elongate member 118. In addition, in some embodiments, portions of the base 90 may be formed integral with the body 20. For example, the body 20 may include the shroud 98 and the base 90 may fit substantially within the body 20.

The assembly of the connector 10 will now be described. In some embodiments, the connector 10 can be assembled by slidingly coupling the seal 60 onto the base 90 by inserting the proximal end, or tip portion 92 end, of the elongate portion 118 into the seal distal opening 82 so that the elongate portion 118 receives the seal 60. The support annular channel 108 can receive the seal distal end 78, and the seal distal face can engage the seal step 122. The elongate portion 118 or the inner surface of the seal opening 82, or both, can be coated with a lubricant prior to assembling the seal 60 onto the elongate portion 118 to facilitate sliding engagement between one another. The seal proximal end 62 and the elongate portion 118 can be inserted into the body 20 distal opening 30. The seal and elongate portion can proximally engage the body cavity 42.

The seal 60 can be configured to have a minimal internal volume, or gap, between the elongate member proximal tip 92 and the seal proximal flange face 63 in the assembled configuration. Particularly, the internal volume adjacent the proximal end 62 can be minimized. The minimal internal volume, or gap, can decrease the retrograde, or backflow, effects of syringe removal from the connector 10. The backflow effect can occur because of the withdrawal of the volume of the elongate portion 118 tip 110 from the slit 70, whereby the fluid is drawn into the volume previously occupied by the tip 110.

The body 20 and base 90 are lockingly engaged longitudinally, or axially, by the body annular channel 38 receiving and engaging, in a snap fit type manner, the base annular protrusion 96. The body 20 and base 90 are lockingly engaged circumferentially by the body channels 40 receiving and engaging the base protrusions 112. The body member 20 and the base member 90 can be further coupled together with adhesive, plastic or sonic or laser welds, snap, interference, or press-fit features, or by using any other suitable coupling features or methods. In some embodiments, the body member 20 and the base member 90 can be coupled together using sonic welds having a substantially triangular shape, although other shapes may also be suitable.

Upon assembly of the connector 10, the seal 60 is in an extended, closed valve position. In the extended position, the seal 60 is generally still compressed because of the retaining contact between the seal prongs 72 and the body shoulder 36. In some embodiments, the seal 60 can be fully expanded when making contact with the shoulder 36 and having the proximal flange face flush to the body proximal face 34. The connector 10 can include a flow path that enters at the body 20 proximal opening 28 into the body cavity 42. Fluid flow proceeds from the cavity 42 into and through the radial openings 100 disposed at the proximal tip portion 92 of the elongate portion 118. In some embodiments, fluid does not enter the cavity 42 directly, as an inserted medical implement, such as a syringe, can directly and sealingly engage the seal proximal face 63, and distally depress the seal 60 proximal face to establish fluid communication with the radial opening 100 of the elongate member 118 and the conduit 102. Thus, the fluid would flow from the syringe into the radial opening 100 and conduit 102. The internal blunt cannula, or elongate member 118, can create a unique dedicated internal fluid path such that at no time can the body 20, the outer surface of the seal 60, or the outside of the syringe come in contact with the fluid or the fluid path. The sealing engagement between the syringe and the seal proximal flange face 63 defines a safe and effective microbial barrier that reduces bacteria transfer into the fluid flow path. The sealing engagement can protect the vascular access device against intraluminal bacterial contamination.

The conduit 102 and seal 60 can combine to define an ultra low residual volume, or deadspace, which provides several advantageous effects. The ultra low residual volume establishes a neutral displacement that can eliminate blood or fluid backflow into the catheter when the upstream medical implement is disconnected from the connector. A saline flush can be performed to provide for reuse following blood sampling or administration of fluids with normal saline or in accordance with facility protocol, facilitated by little or no blood backflow induced by the connector. The neutral displacement also allows for effective flushing after using the connector with blood, to flush the blood out of the connector flow path in the conduit 102. Neutral displacement also can preclude the need for a clamping sequence of the conduit 212 that enters the patient. Additionally, the lack of backflow can eliminate the educational burden and risk of error for medical personnel. The minimal volume to flush the connector to remove blood or medicament fluid from the from connector 10 can allow continued use of the connector 10 without having to remove or replace the connector. This can reduce the amount of manipulation of the connector 10, where removal and replacement of the connector 10 can increase the risk of bacterial contamination.

The fluid can flow through the elongate portion 118, in conduit 102, to the distal opening 114 of the male protrusion tip 116. The base 90 distal end 124 can be coupled to a distal, or downstream, medical implement that is coupled to the luer fitting and threads 128 on the inside surface 130 of the shroud 98. Thus, the fluid can exit the connector 10 at the distal opening 114 and continue into the downstream, or distal, medical implement. The substantially transparent body 20, seal 60, and elongate portion 118 can provide a substantially clear view of the fluid flow within the connector 10 during medicament delivery or bodily fluid extraction. Visual awareness, or inspection, of potential contamination of the plurality of cavities in the connector 10 can reduce the risk of potential harm to the patient, e.g. bacterial growth or biofilm due to stagnant or residual fluid or the like, by prompting immediate cleaning or flushing of the connector 10 or removal and replacement of the connector 10. For example, the visual inspection can prevent catheter related bloodstream infections such as catheter sepsis that can be caused by residual blood in the needlefree connector 10.

The connector 10 valve mechanism is closed when the seal 60 extends proximally over, and encompasses, the elongate portion 118. In some embodiments, the inward bias of the adjacent edge surfaces of the seal slit 70 cause the edges surfaces to coapt and prevent fluid or particulate access to the internal volume of the seal 60, and thus to the fluid flow path of the radial openings 100. The valve mechanism of the connector 10 can be urged into an open position by distally displacing the seal 60 to slide in a distal direction. The proximal end, or first end, of the seal 60 can be positionable between a first position and a second position. The proximal portion, or first end, of the elongate portion 118, can be disposed substantially within the proximal end of the seal 60 when the seal is in the first position. The elongate portion 118 can protrude through the seal slit 70 as the seal proximal end 63 moves distal of the tip portion 92. Upon such distal movement, the proximal portion, or first end, of the elongate portion 118 can be disposed substantially outside of the proximal end of the seal 60 when the seal is in the second position. The fluid flow path is open when the seal proximal face 63 material, and the slit 70, have moved distally past the radial openings 100 to expose the radial openings 100 to the internal surface of the syringe. The radial openings 100, or apertures, facilitate fluid communication to the fluid flow path when the valve is in the second position. When the syringe distally urging implement, or force, is relieved from the seal 60, the resilient bias of the seal extends, or decompresses, or expands, the seal to an increased longitudinal length whereby the seal slit 70, or septum, encompasses the radial opening 100 and the tip portion 92 to close the connector 10 valve mechanism.

Some embodiments of the connector 10 can be formed so that there is very little dead space volume, or a neutral displacement as discussed above, within the connector 10 as compared to the volume range of a typical bolus of fluid administered to a target patient population. Thus, the volume of fluid entering into the connector 10 can be substantially equivalent to the volume of fluid leaving the connector 10. Further, the total equivalent fluid volume of the connector 10 can be very small, e.g. 0.02 cc, 0.04 cc, or the like, such that the volume of fluid flowing through the system in order to place the valve in fluid communication with a medical implement such as a syringe can be very close or equal to zero. A small volume of dead space within the fluid flow path reduces, or mitigates, the vacuum effect that generates negative flow when the syringe is removed from the connector 10. The volume of dead space can be limited to the air gap in the inner volume of the proximal end 62 of the seal 60. The small volume between the tip 110 and the seal proximal face 63 advantageously can create minimal, if any at all, negative flow effects from the catheter into the distal end of the connector 10.

In some embodiments, the support member may be substantially shorter, such that it does not extend into, through and/or near the proximal end of the seal. In some embodiments of the connector 10, there is no support member at all. A seal member can be configured to open without a penetrating support member or without a support member at all, such as when a seal member is made in a naturally open position that is forced to close by a smaller-diameter housing, or when a seal member is attached to the proximal region of the housing, etc. Alternatively, the support member may not be rigidly fixed in the housing. Rather, it may be held in the housing via a resilient seal and may translate longitudinally upon insertion of a medical device into the proximal end.

With reference to the illustrated embodiments of FIGS. 6-10, the operation of an example of connector 10 will now be described. FIG. 6 illustrates the position of the components comprising the connector 10 when the seal member 60 is biased in the closed position, e.g., before a syringe or other medical implement has been joined with, or inserted into, the connector 10.

FIG. 6 is a section view of the embodiment of the connector 10 shown in FIG. 2A, showing the seal member 60 in a first or closed position, e.g., before the seal member 60 has been contacted and opened by insertion of a luer, such as a luer on a syringe 200. FIG. 7 is a section view of the embodiment of the connector 10 shown in FIG. 2A, showing the seal member 60 in a second or open position, e.g., after the seal member 60 proximal face 63 has been contacted and opened by insertion of a luer, such as a luer on the syringe 200. The syringe cannula 204 can engage the seal proximal face 63 and establish a fluid-tight seal between the cannula and the seal proximal face 63, such that all the fluid from the syringe transfers to the elongate portion 118 fluid conduit 102. In this manner, the fluid remains in the flow path of the conduit 102 and can stay out of the cavity 42, or the volume between the seal 60 outer surface and the body inner surface 44. In progressing between the closed and opened positions, the seal member 60 can be configured to move under a distally directed load on the seal proximal end 63, such as by pressing the syringe distally against the seal 60. The syringe 200 is distally urged with suitable force to overcome the bias resiliency of the seal 60. In some embodiments, as illustrated, the seal member 60 can be compressed in the open position and expanded or allowed to return to its initial position in the closed position. In some embodiments, the seal member 60 has a smaller longitudinal length in the open position than in the closed position. Many other types of seal members can be used to open and close the fluid passage within the connector in many different ways. The seal member 60 can be positioned within the connector 10 so that a proximal end surface 63 of the seal member 60 is generally flush or generally even with a proximal end opening of the connector 10 to permit effective antiseptic wiping across the proximal end surface 63.

The syringe 200 illustrated in FIGS. 6-10 is an example of one type of medical implement that can be used with the connector 10. However, the connector 10 can be configured for use with a wide range of medical implements and is not limited to use with the example of the syringe 200 illustrated. The syringe 200 can be any suitable or common medical syringe used in the medical field. As illustrated, the syringe 200 can have a cylindrical body portion 206 defining an opening therein, a hollow cannula 204 projecting from the body portion 206, and a plunger 202 configured to be received and axially translate within the opening formed in the body portion 206. The plunger 202 can have an elastomeric or rubber seal 208 supported on the end of the plunger 202. As is commonly done with such medical syringes, fluid can be expelled from the syringe 200 by forcing the plunger 202 toward the bottom surface 211 of the body portion 206, thus causing the fluid to exit through the hollow cannula 204. In this manner, the fluid is typically expelled from the syringe 200 until the rubber seal 208 of the plunger 202 reaches the bottom surface 211 of the syringe 200.

In order to inject all or substantially all of the fluid held within the syringe 200 into the patient's vasculature, a caregiver or automated machine will typically depress the plunger 202 of the syringe 200 or other mechanism all the way into the body member 206 until the plunger 202 and the rubber seal 208 bottoms out against the bottom surface 211 of the syringe 200, which can cause the typically resilient rubber seal 208 to be compressed between the generally rigid plunger 202 and the bottom surface 211 of the syringe. When this occurs, the seal 208 on the end of the plunger 202, which is typically made from a rubber or other resilient material, can rebound when the force exerted by a caregiver on the plunger 202 is removed.

FIG. 7 illustrates the seal member 60 in an open position in response to the insertion of the syringe 200 being joined with the connector 10. As illustrated in FIG. 7, the luer or cannula 204 of the syringe 200 or other medical implement has been pushed distally against the seal member 60 with sufficient force to overcome the bias of the seal member 60 so as to cause the seal member 60 to compress or otherwise move within the body member 20. The seal member 60 is moved distally and the elongate portion tip 110, and tip portion 92 penetrates, opens and separates the coapted edges of the slit 70. When the seal member 60 is compressed within the body member 20 to a sufficient distance such that the proximal end surface 63 of the seal member 60 has moved distal of the radial openings 100 formed in the elongate portion 118 of the base 90, the opening 114 and/or the conduit or passageway 102 is in fluid communication with the inside of the syringe 200.

The force that the cannula 204 exerts on the end surface 63 of the seal member 60 can be sufficient to cause a substantially fluid-tight seal between the cannula 204 and the seal member 60 end surface 63, so that all or substantially all of the fluid within the syringe 200 is caused to flow into the opening 100 when the syringe 200 is joined with the connector 10 in this compressed seal 60 manner. In some embodiments, the elongate member 118 does not pierce or penetrate the seal 60. For example, in some embodiments, the elongate portion 118 comes into close proximity with (e.g., in contact with, adjacent to, or positioned very near) the interior surface of the top of the seal member when the connector 10 is opened without entering or going through the slit 70 of the seal 60. In some embodiments, the seal member 60 can be configured to have a naturally open position, without requiring the elongate portion 10 to open the seal member 60.

Thus, when the seal member 60 is in the open position, as illustrated in FIG. 7, the plunger 202 of the syringe 200 can be depressed so as to force fluid into the connector 10. In some embodiments, when fluid is forced from the syringe 200, fluid can flow into the opening or openings 100 formed in the elongate portion 118 of the base 90, through the passageway 102, and through the opening 114 formed in the base 90. As discussed, when the syringe 200 or other medical implement is removed from connector 10, the connector 10 can be configured such that the seal member 60 can return to the closed position due to the bias force within the seal member 60.

Figure 7A:
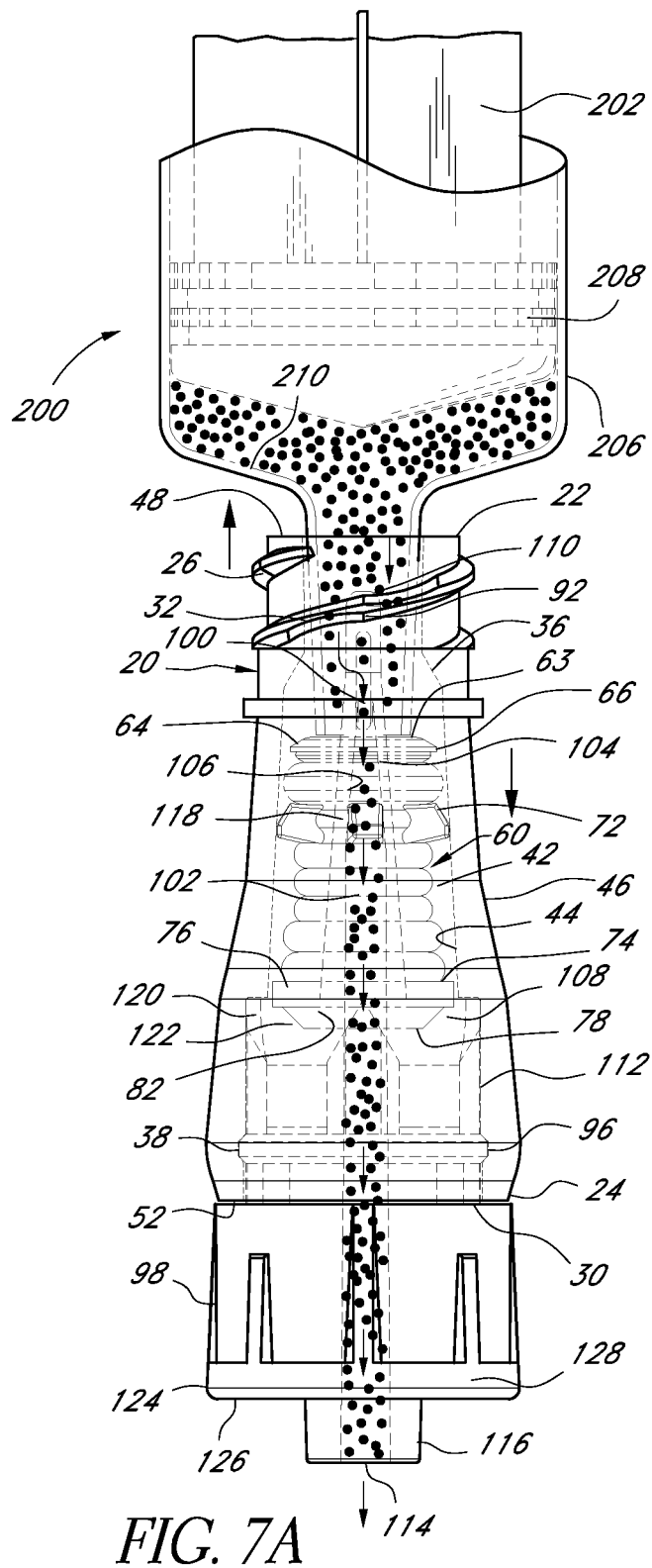
FIG. 7A is a front view of the embodiment of the connector shown in FIG. 2A, showing the seal member in an open position and fluid flow visible through the transparent walls of the body, seal, and support.

In the illustrated embodiment of FIG. 7A, the transparent feature of the open valve configuration of FIG. 7 is shown. The syringe 200, seal 60, elongate portion 118, and the fluid medicament are visible through the transparent wall of each component. The transparent body 20 advantageously provides a substantially clear visual observation of the regions within the connector 10 where the fluid medicament or bodily fluid flows during use. The syringe cannula 204 generally will self-align in the neck 32 portion of the body 20 proximal end, and make flat and even sealing engagement with the seal proximal face 63.

Medical personnel periodically flush connectors and intravenous tubing with saline, especially after administration of medications and drawing of blood. The saline flush serves to ensure that the full dose of medication is given to the patient and that there is also no residual blood left in the tubing or connector. Residual blood in the connector may clot and/or become a source of bacterial contamination. Because a connector is used to introduce fluids intravenously, contamination can be introduced to the patient rapidly causing systemic infection. Thus further advantages of a transparent connector 10 include enabling medical personnel to detect subtle changes in the appearance of the saline left in the intravenous line such as blood clots, as well as turbidity or cloudiness which may be an indication of connector contamination. A connector leak may go undetected if the leak is in a non-transparent region of the connector 10. Embodiments of the connector 10 described herein have the added advantage of exposing all connector components to visual inspection, thus assuring medical personnel that the connector 10 is functioning correctly at all times. The transparent connector 10 also allows medical personnel to readily assess the efficacy of the flush because residual fluid that remains in the connector can be clearly visible. In some embodiments, the body 20 material can include components that magnify the flow path region, which makes the flow path visual appearance larger and readily visible.

In the event that even sealing engagement is not made between the syringe 200 and the seal 60, fluid may spread into the body cavity 42, or between the seal 60 and the inner portion 118, rather than flowing directly from the syringe into the elongate portion 118 radial openings 100. Medical personnel administering the medicament can immediately observe the leaking fluid and address the leak by, for example, stopping the medicament administration, and/or by cleaning, flushing or removing and replacing the connector 10 after the medicament is administered. The ability to monitor the fluid levels and location provides a real-time assessment of the effectiveness and non-leak success of the fluid transfer. Knowledge of whether any of the the transfer fluid either remains in the fluid conduit or has escaped from the primary internal fluid conduit allows timely flushing and/or replacement of a connector that is contaminated, or at high risk of contamination due to undesirable residual fluids. The ability to quickly respond to fluid in the generally non-fluid flow cavities reduces the potential risks to the patient due to fouled lines, conduits, medical connectors, or other medical implements.

Figure 8:
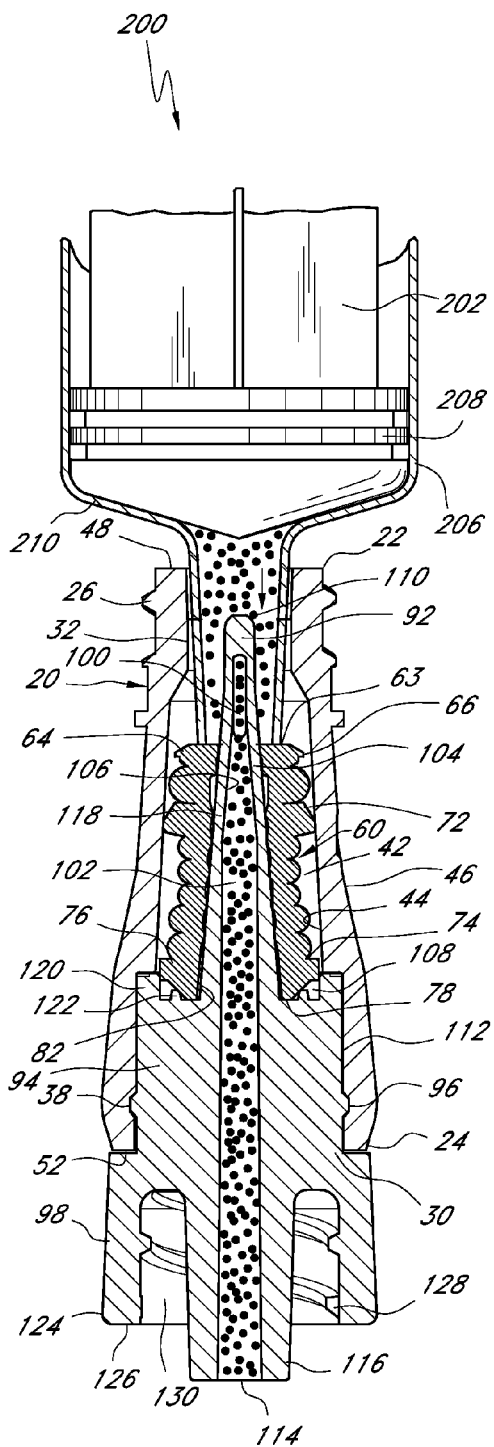
FIG. 8 is a section view of the embodiment of the connector shown in FIG. 2A, showing the seal member in an open position and the plunger of the syringe advanced to the bottom surface of the syringe.

FIG. 8 is a section view of the embodiment of the connector 10 shown in FIG. 2A, showing the seal member 60 in an open position and the plunger 202 of the syringe 200 compressed against the bottom surface 211 of the syringe 200. As illustrated in FIG. 8, medical personnel that administer the fluid in the syringe 200 to a patient typically depress the plunger 202 against the bottom surface 211 of the syringe so as to expel substantially all of the fluid from the syringe into the connector, causing the commonly resilient seal 208 on the end of the plunger 202 to compress between the substantially rigid plunger 202 and the substantially rigid bottom surface 211 of the syringe.

Figure 9:
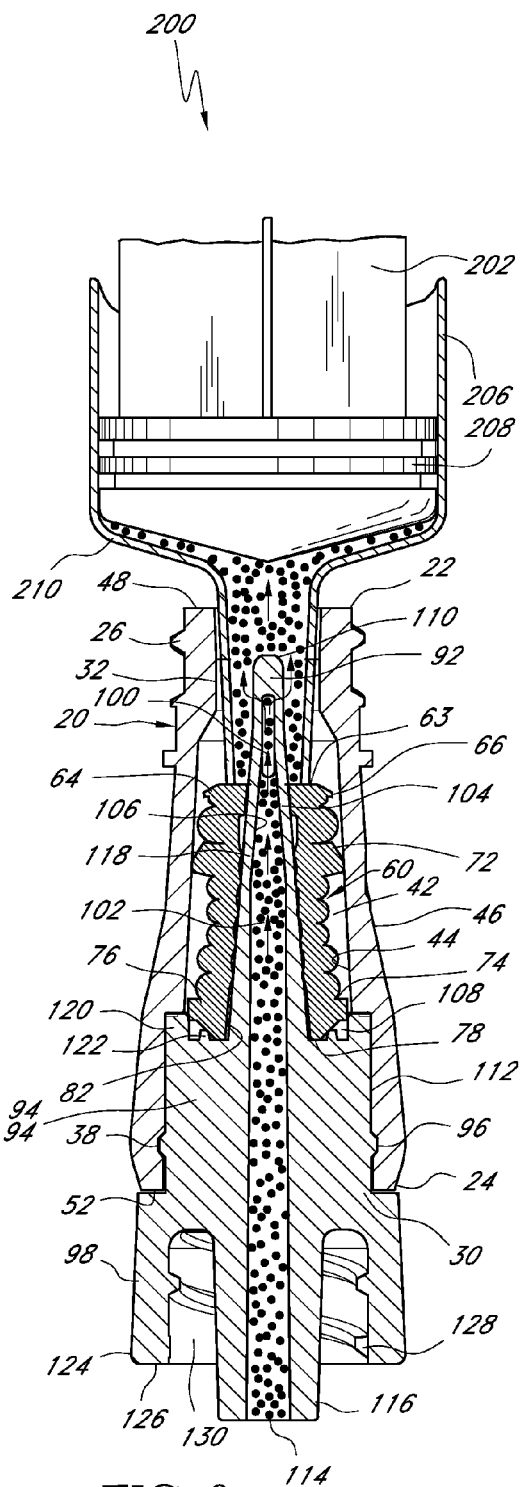
FIG. 9 is a section view of the embodiment of the connector shown in FIG. 2A, showing the seal member in an open position and the syringe after the plunger of the syringe has rebounded away from the bottom surface of the syringe.

In this position, when the plunger 202 has been completely depressed relative to the syringe 200 such that no additional fluid is being forced from the syringe 200, the fluid flow within the syringe 200 and, hence, the connector 10, stops. FIG. 9 is a section view of the embodiment of the connector 10 shown in FIG. 2A, showing the seal member 60 in an open position and the syringe 200 after the syringe plunger 202 has rebounded away from the bottom surface 211 of the syringe 200. After the rubber seal 208 on the end of the plunger 202 has been depressed against the bottom surface 211 of the syringe 200 such that substantially all of the fluid has been expelled from the syringe 200 and the caregiver releases the plunger 202, the resilient seal 208 on the end of the plunger 202 typically causes the plunger 202 to rebound away (as illustrated) or expand upward from the bottom surface 211 of the syringe. When this occurs, a volume of space is created between the seal 208 and the bottom surface 211 of the syringe 200, causing a vacuum to be created in the syringe 200.

Figure 10:
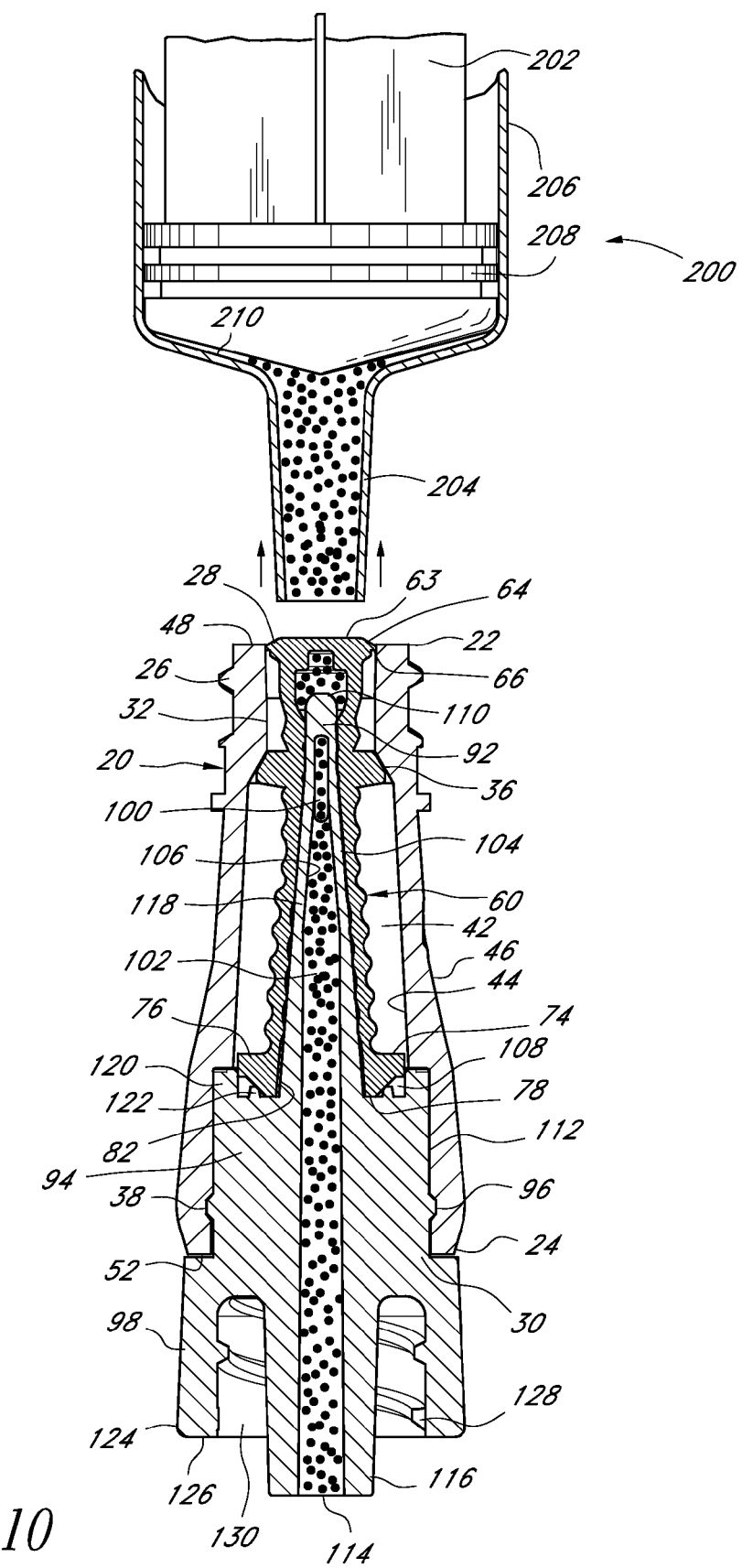
FIG. 10 is a section view of the embodiment of the connector shown in FIG. 2A, showing the seal member in the first position after the syringe has been removed from the connector.

In the illustrated embodiment of FIG. 10, the connector 10 is shown after the syringe 200 is removed from the connector. After the desired amount of fluid has been dispensed from the syringe 200 or other medical implement, the syringe 200 or other medical implement can be removed from the connector 10. When the syringe 200 or other medical implement is removed from connector 10, the connector 10 can be configured such that the seal member 60 can return to the closed position due to the bias force within the seal member 60. This reversibility of the seal member 60 makes the connector 10 particularly attractive as a connector valve to provide fluid communication between two fluid lines. Since the connector 10 can be sealed closed and can be disinfected, various syringes or medical implements can be easily joined with the connector 10 multiple times without requiring removal of the connector 10 from communication with the patient's vasculature. Fluid can be present in the small volume of the seal proximal end 62, positioned proximal to the elongate portion 118, as well as in the internal volume of the elongate portion 118.

Figure 10A:
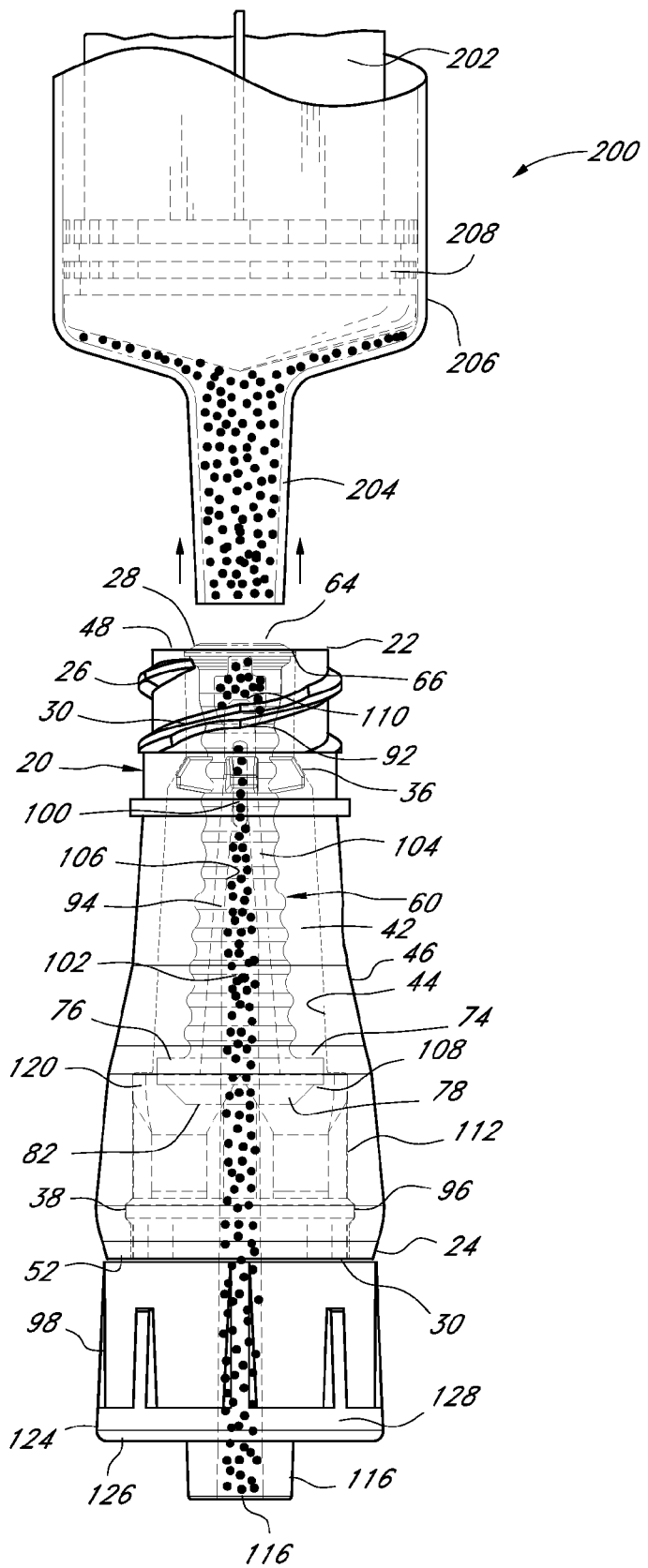
FIG. 10A is a front view of the embodiment of the connector shown in FIG. 2A, showing the seal member in the first position after the syringe has been removed from the connector.

In the illustrated embodiment of FIG. 10A, the transparent feature of the connector 10 of FIG. 10 is shown. The transparent body 20, seal 60, and elongate portion 118 provide a substantially clear visual representation of where the medicament fluid which exited the syringe 200, or medical implement, has dispersed within the cavity 42, and/or the seal 60, and/or the elongate portion 118 and fluid conduit 102 of the base 90. Fluid observed in the cavity 42, between the seal 60 and the inner surface 44 of the body 20, can indicate a lack of sealing between the syringe 200 and the seal proximal face 63, and can generally result in cleaning/flushing the cavity 42 in accordance with facility protocol or replacement of the connector 10.

In the illustrated embodiments of FIGS. 11-19A, another embodiment of a valve or needleless connector 210 is shown. In some embodiments, the connector 210 can have any of the features or other details or configurations of any other connector described herein, including but not limited to connector 10. Throughout the drawings, reference numbers can be re-used to indicate correspondence between referenced elements. Like reference numbers indicate identical or functionally similar features. Similarly, corresponding features can be identified by commonality of the last two digits of the reference numbers, e.g. connectors 10 and 210 can have similar features.

With reference to FIGS. 11-19A, in some embodiments, the connector 210 can comprise a body member 220, a seal member 260, and a base member 290. The connector 210 can further include a support member 294 that is independent of the base 290, and a second valve member 350. The support member 294 is not integrally coupled and does not form a part thereof of the base 290. The second valve, or regulator 350, can be operative as a valve mechanism configured to achieve negative flow compensation effects to prevent fluid backflow from conduit 212 and stop fluid from being drawn back into the connector 210.

As similarly described above, the body member 220 can include a proximal end 222, a distal end 224, external threads 226, a proximal opening 228, and a distal opening 330. The body 220 can further include a neck 232, a shoulder 236, an annular channel 238, an internal surface 244, an outer surface 246, and a distal flange 252. These body 220 features include similar characteristics to the features described herein with respect to body 20. The seal member 260 correspondingly has characteristics similar to seal 60 described herein, such as a proximal end 262, flange face 263, lip 266, slit 270, prongs 272, flange 274, convolutes 280, distal opening 282, and middle portion 284.

As similarly described above, the body member 220 and the base member 290 can be joined together to provide a rigid housing that substantially encapsulates the seal member 260, the support member 294, and the regulator 350. The body member 220 and the base member 290 can be joined together using any suitable method or features, including but not limited to the methods or features described elsewhere herein for joining the body member 20 with the base member 90. The body 220, the seal 260, the support 294, the elongate portion 318, and the base 290 can be comprised of transparent material that provides a substantially clear view through the walls of each component of the connector 210. The tip portion 292 can be transparent through the outer surface 304 and the inner surface 306 such that an internal fluid disposed within the tip portion is visible. The transparent characteristics of the body 220, the seal 260, and elongate portion 318 provide a direct and substantially clear optical visual, or view, of the medicament fluid flow from a medical implement through the connector 210. Medical personnel can observe a medicament administered to a patient with optical clarity and readily determine issues or risks encountered due to fluid leakage past seal 260, backflow into the connector 210, blocked flow, or contamination in the connector.

Figure 12:
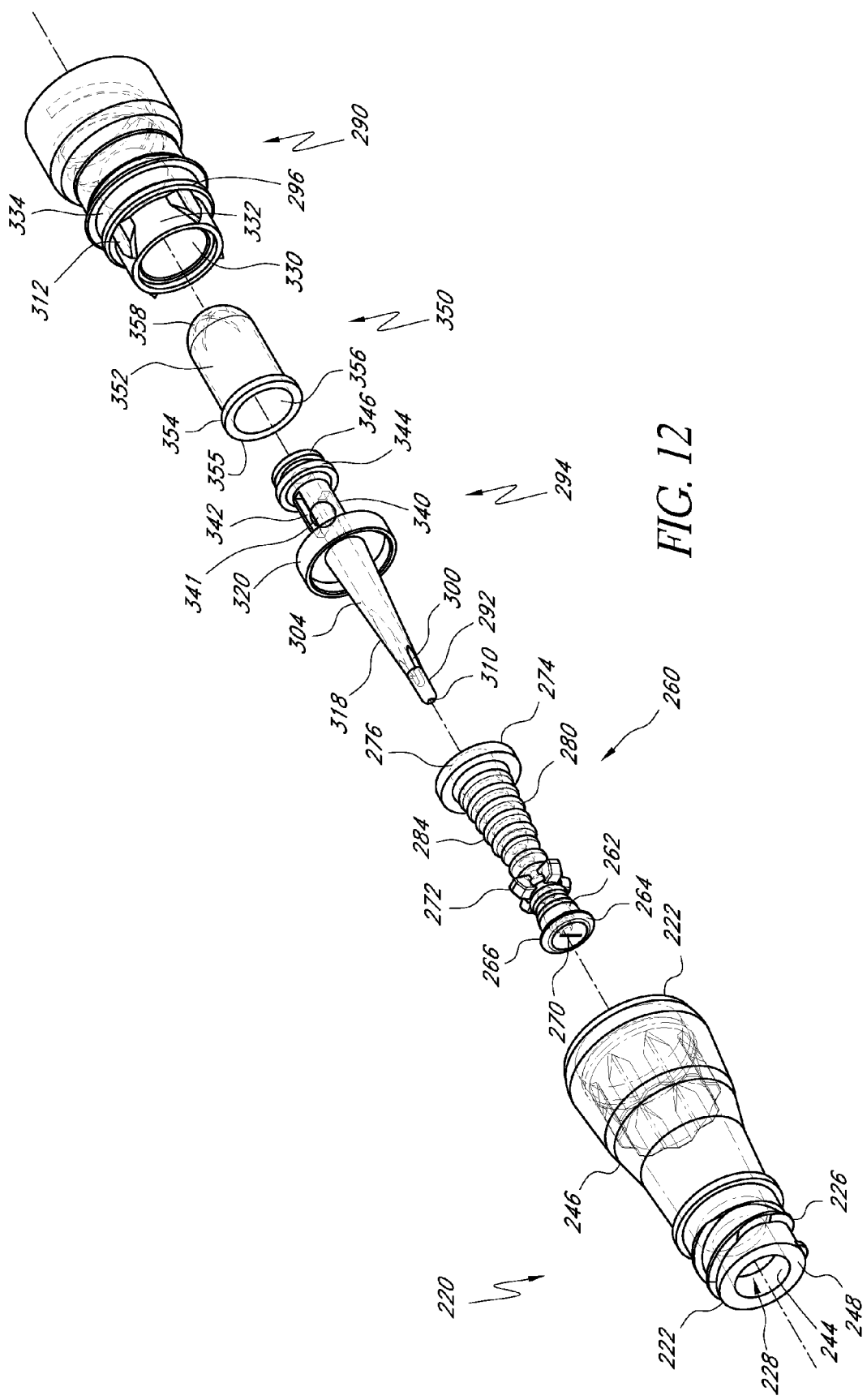
FIG. 12 is a proximal exploded view of the embodiment of the connector shown in FIG. 11A.
Figure 13:
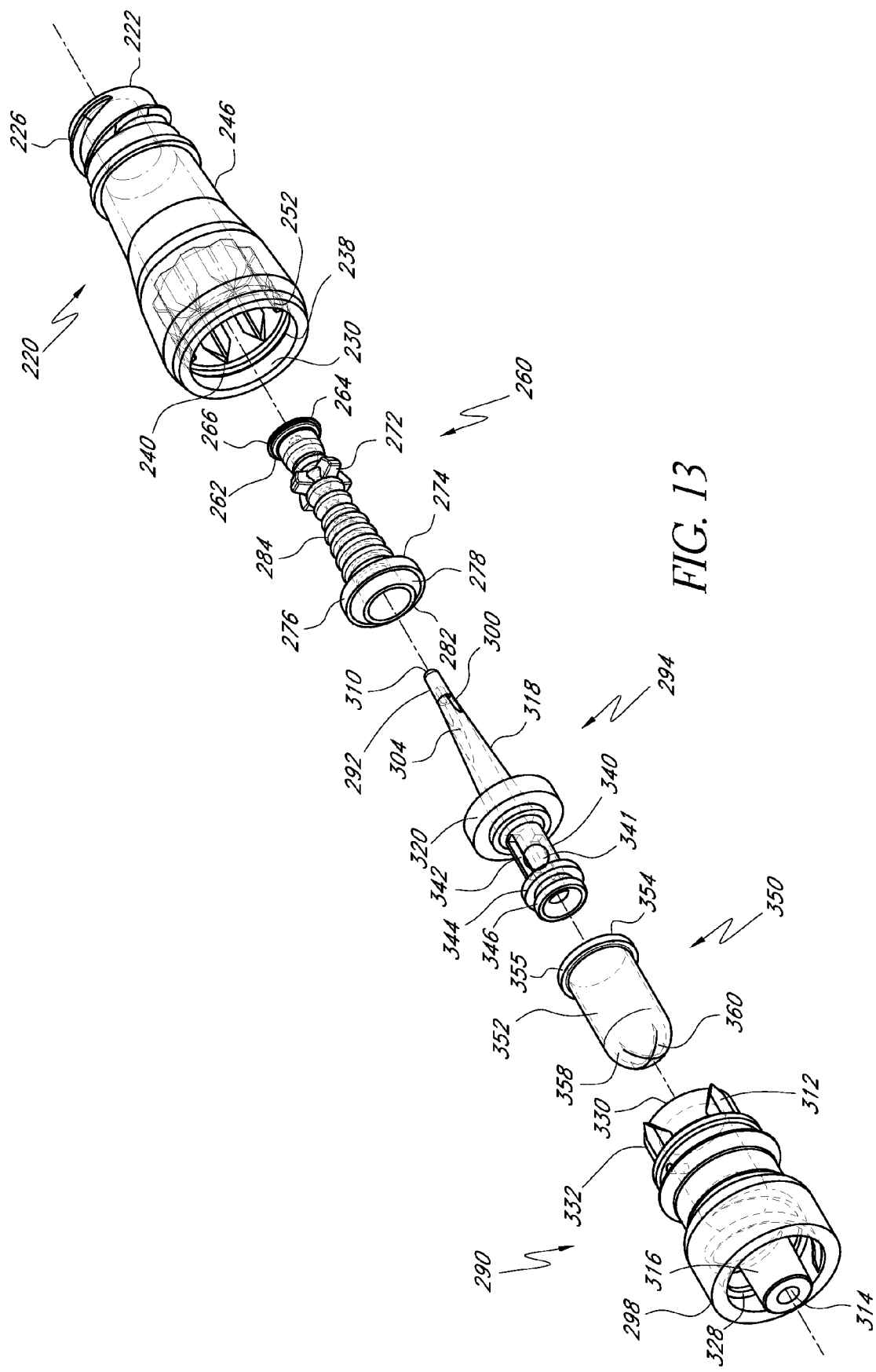
FIG. 13 is a distal exploded view of the embodiment of the connector shown in FIG. 11A.
Figure 14:
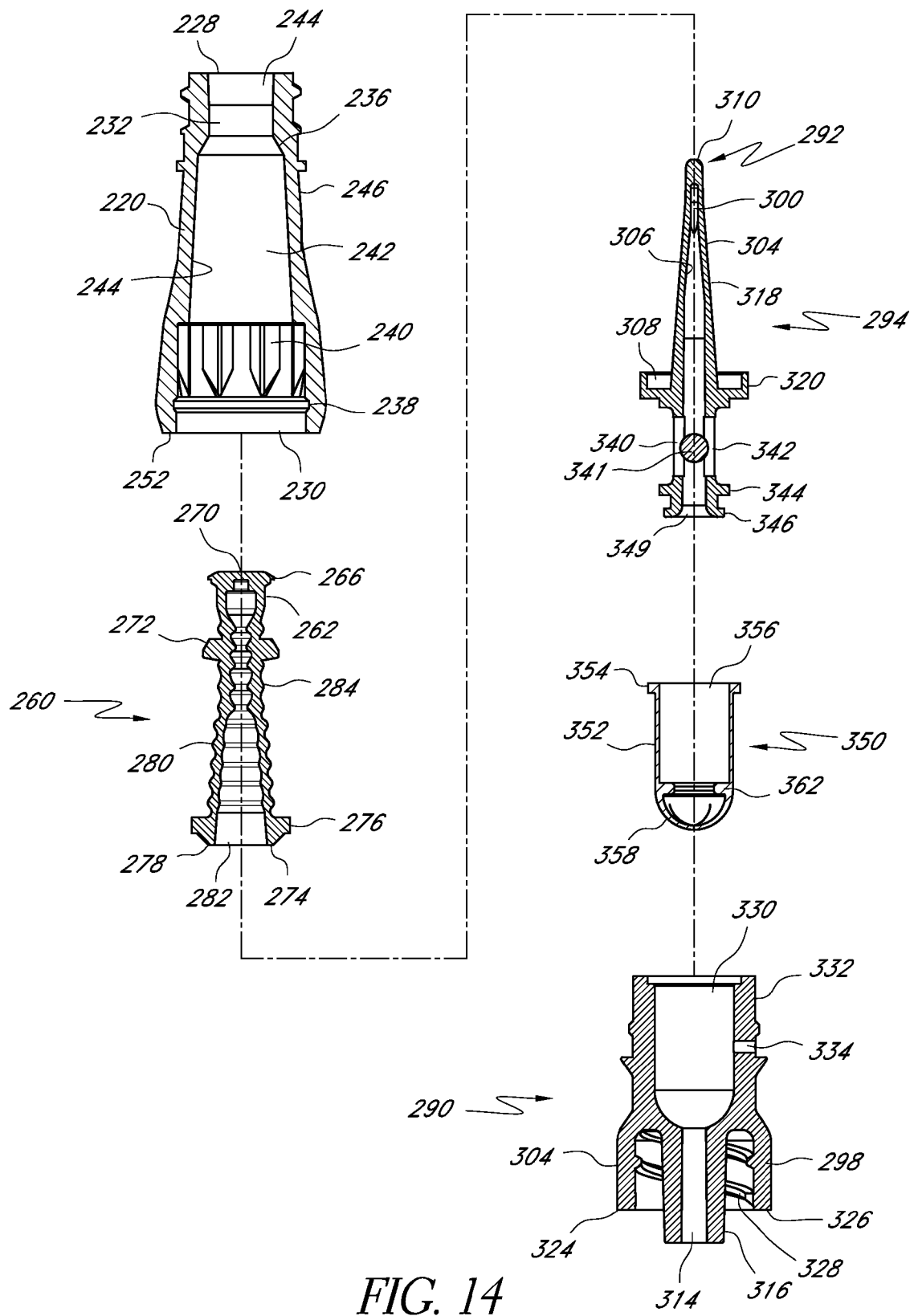
FIG. 14 is an exploded section view of the embodiment of the connector shown in FIG. 11A, taken through the axial centerline of the connector.

FIGS. 11-13 are assembled and exploded perspective views of an embodiment of the connector 210. FIG. 14 is a section view of the connector 210 shown in FIGS. 11-13, taken through the axial centerline of the connector. FIGS. 15-19 illustrate a method of using the connector 210. The regulator 350, the support 294, and the base 290 are described in detail below.

As illustrated in FIGS. 12-14, the regulator 350 can have a body portion 352, a proximal end 354, a lip 355, an opening 356, a valve 358, and at least one slit 360. In some embodiments, the body portion 352 can be generally cylindrically shaped, the lip 355 can be an annular raised portion on the proximal end 354, and include the opening 356 extending therethrough. The regulator 350 can be configured to control fluid flow through and/or within the connector 210. The regulator 350 can provide a variable-volume or dynamic regulator portion wherein the body 352 has thin, flexible, compliant side walls that can be highly responsive to fluid pressure changes. In some embodiments, the thin side wall can be substantially thinner than the side wall of at least a portion of, or virtually the entire, side wall of the seal member 260 to enable the regulator 350 to be highly responsive to fluid pressure changes.

The regulator 350 can include the valve 358 that is defined by the slit 360 disposed on the dome shaped, or arcuate, geometry of the regulator distal end. The valve 358 regulates fluid flow through the connector 210 male tip protrusion 316 and the radial opening 300. The slits 360 can include one or a plurality of apertures through the regulator 350 distal end, and can be in any general arrangement, e.g. crossed, triangular, centered, offset, or the like. The slits 360 can be biased toward one another in a closed configuration that prevents fluid flow through the connector. The slits 360 can be configured to open and allow flow only after a predetermined selective pressure differential threshold is attained between the regulator body 352 interior volume and the distal pressure in the connector base 290 or the conduit 212. The slits 360 have a higher resistance to deflection induced by pressure differentials across the regulator distal wall thickness than the thin walled portion of the regulator body 352.

The regulator 350 can compensate for negative flow effects, e.g. during syringe removal from the connector, or syringe seal springback. The thin walls of the regulator body 352 can deflect radially inward when the proximally directed vacuum pressure effect occurs. The slits 360 can be configured to not deflect or only minimally deflect under the same pressure effect. In this way, the thin walls of body 352 deflect and compensate and absorb the pressure differential while the fluid downstream of, or distal to, the regulator slits 360 experiences little or none of the pressure effects that can draw fluid into the connector 210 or from the patient into the conduit 212. The slits 360 can deflect when a sufficient pressure differential exists and proximally directed fluid flow is intended, such as when blood is drawn from the patient. The slits 360 can also be configured to provide a greater resistance to proximally directed flow, and a lesser resistance to distally directed flow. The lesser distal flow resistance provides ease of delivery of medicament from a syringe through the connector 210 to the patient.

The regulator 350 or any other embodiment of a regulator, valve, or valve member disclosed herein and any of the components or features thereof can be constructed from a number of different materials, including silicone-based deformable materials, rubbers, or other suitable materials. Silicone-based deformable materials are among those that form fluid-tight closures with plastics and other rigid polymeric or metallic materials. In some embodiments, the regulator 350 can be flexible, elastomeric, and/or resilient. In some embodiments, the regulator 350 can be made from the same material as the seal member 260.

The support 294 includes some features that are similar to base 90 described above. These features include an elongate portion 318, a tip portion 292, a tip 310, a radial opening 300, and an annulus 308. The support 294 differs in that the support is not integrally formed with the base 290, and includes a distal portion 340 configured to engage the second valve, or regulator 350.

The support 294 distal portion 340 can extend distally from a seal support wall 320. The distal portion 340 can include a hollow interior that forms a part of the conduit 302 of the elongate portion 318, and extends to a distal opening 349. The distal portion 340 can include two axially spaced radially outward directed annular protrusions 344, 346, and at least one opening 342 generally positioned between the wall 320 and the protrusion 344. In the illustrated embodiment of FIGS. 11-19A, two radially opposed openings 342 are shown.

The support 294 distal portion 340 is configured to be received in the interior volume of the regulator 350 through the regulator opening 356. A volume 343 is defined between the outer surface of the distal portion 340 and the inner surface of the regulator 350. The volume 343 provides the space for the regulator body 352 thin walls to deflect radially inward when a pressure differential inducing event occurs. Additional details of the negative pressure compensation support 294 and regulator 350 are disclosed in U.S. patent application Ser. No. 12/730,074, which is hereby incorporated by reference in its entirety.

In some embodiments, a diverter 341, or ball, can be disposed within or adjacent the conduit 302 flow path. The diverter 341 is positioned in the flow path and redirects the moving fluid into and toward the volume 343 to preclude stagnant fluid in the volume 343. Thus, the fluid goes around the diverter 341, entering the volume 343 at a first axial position of the diverter 341 and then re-entering the flow path conduit 302 at a second axial position of the diverter 341. In some embodiments, the diverter 341 can have a variety of diameters, e.g. smaller than, the same as, or greater than the inner diameter of the flow path 302. As shown, the diverter 341 is greater in diameter than the flow path 302 and thus is frictionally retained within the openings 342 and conduit 302 inner diameter walls. The diverter 341 can be formed from a generally rigid material such as nylon, or a semi-rigid or flexible material, or any other suitable material, e.g. the same material as the support member 294, or the like. In some embodiments, the flow diverter can have any geometric shape, e.g. rounded, smooth, curved, oval, square, rectangular, triangular, or polygonal, or the like. In some embodiments, the conduit 302 can include a groove or other geometric shape to receive the diverter 341.

In some embodiments, the fluid diverter can interrupt the substantially linear or laminar flow path of fluid between the proximal and distal ends that can otherwise occur inside of the support member 294 and can increase the lateral fluid flow through the volume 343, thereby preventing or diminishing fluid stagnation in the volume 343. In some embodiments, the increased fluid flow through the volume 343 can prevent or diminish the risk of clotting (in the event that blood is transported through the connector 210), bacteria development, or other adverse affects that can result from stagnant fluid inside the connector 210.

The base 290 includes some features that are similar to base 90 described above. These features include protrusions 312, a shroud 298, internal threads 328, a male tip protrusion 316, a distal end 324, a distal face 326, and an opening 314. The base 290 differs in that the base is not integrally formed with the support 294, and includes a cavity 331 defined by inside surface 330 of wall 332 and configured to encompass the second valve, or regulator 350. The base 290 can include one or more openings 334 that can be formed through a portion of the base member 290 to provide an airway between the ambient atmosphere and the outside surface of the body portion 352 of the regulator 350. The base 290 can further include a circumferential slot or groove 329 extending around or substantially around the outer surface of the base member 290 to provide an area of traction to be grasped by an operator. Such a groove also permits a more uniform wall thickness in the area of the base member 290 to enhance the efficiency of manufacture and the transparent characteristics of the connector 210.

Figure 15:
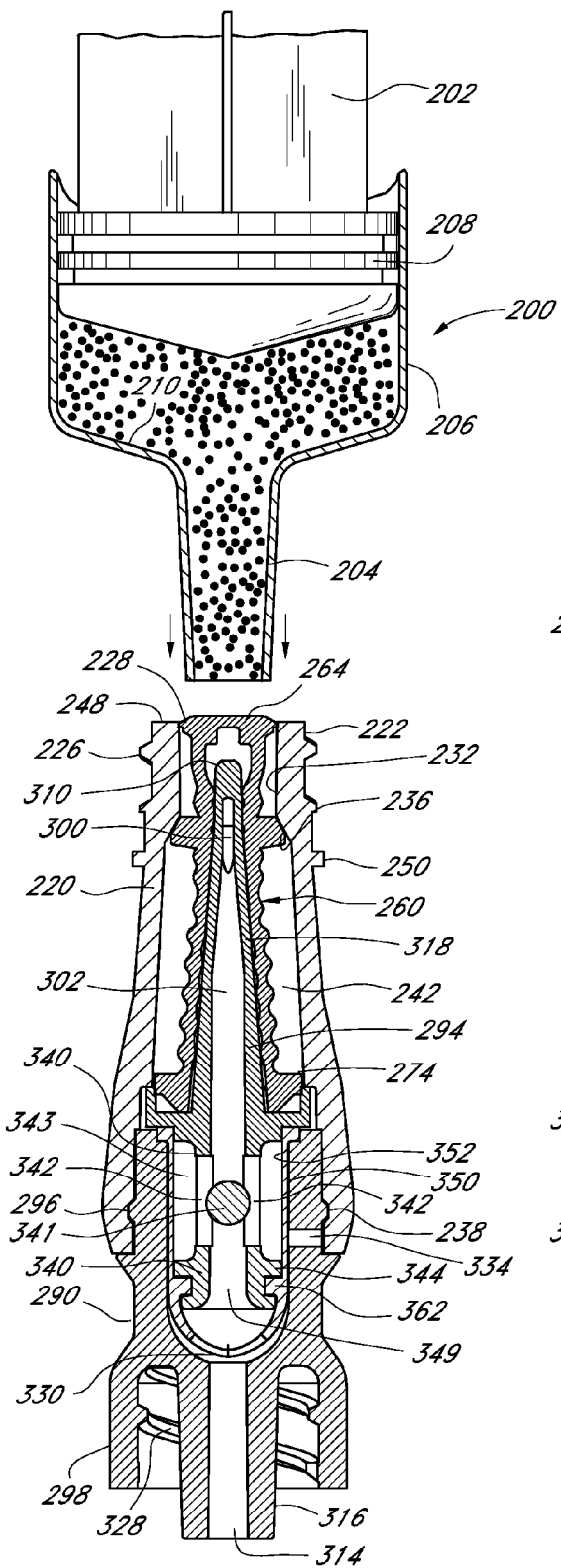
FIG. 15 is a section view of the embodiment of the connector shown in FIG. 11A, showing the seal member in a first or closed position before the seal member has been contacted and opened by the syringe.
Figure 16:
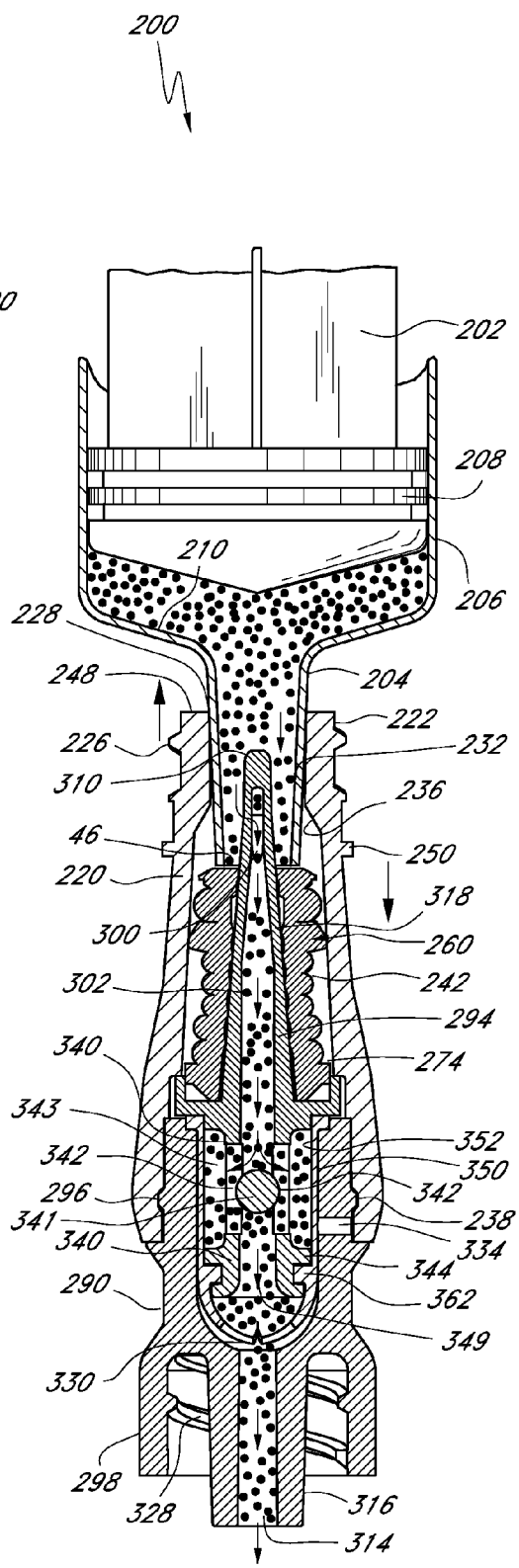
FIG. 16 is a section view of the embodiment of the connector shown in FIG. 11A, showing the seal member in a second or open position after the seal member has been contacted and opened by the syringe.
Figure 17:
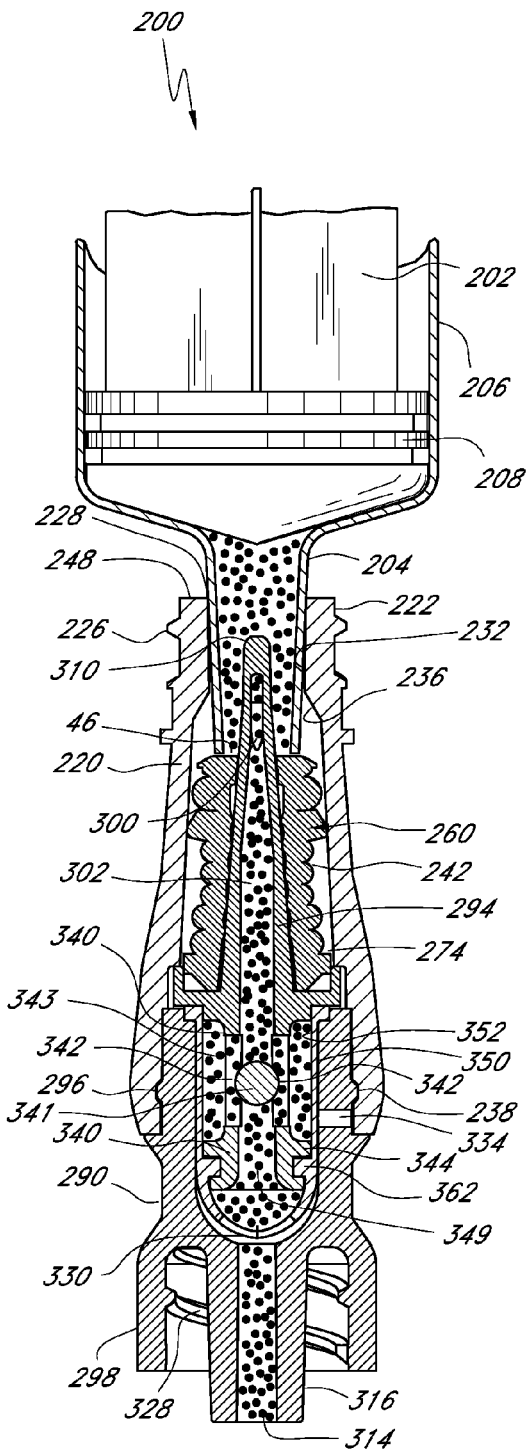
FIG. 17 is a section view of the embodiment of the connector shown in FIG. 11A, showing the seal member in an open position and the plunger of the syringe advanced to the bottom surface of the syringe.
Figure 18:
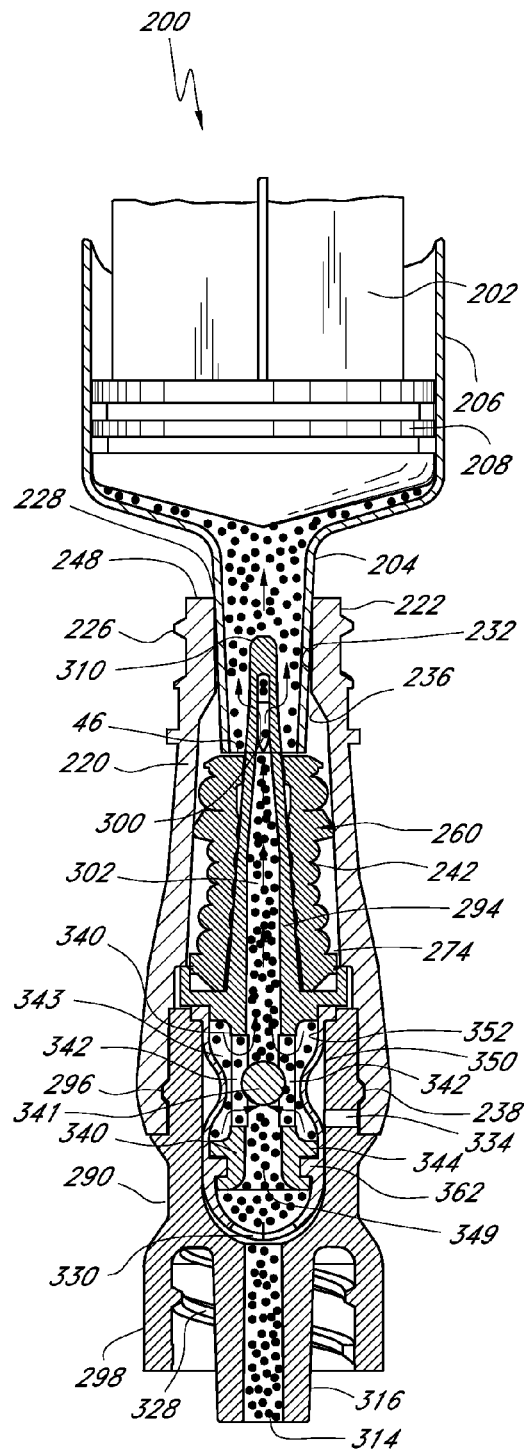
FIG. 18 is a section view of the embodiment of the connector shown in FIG. 11A, showing the seal member in an open position and the syringe after the plunger of the syringe has rebounded away from the bottom surface of the syringe.
Figure 17A:
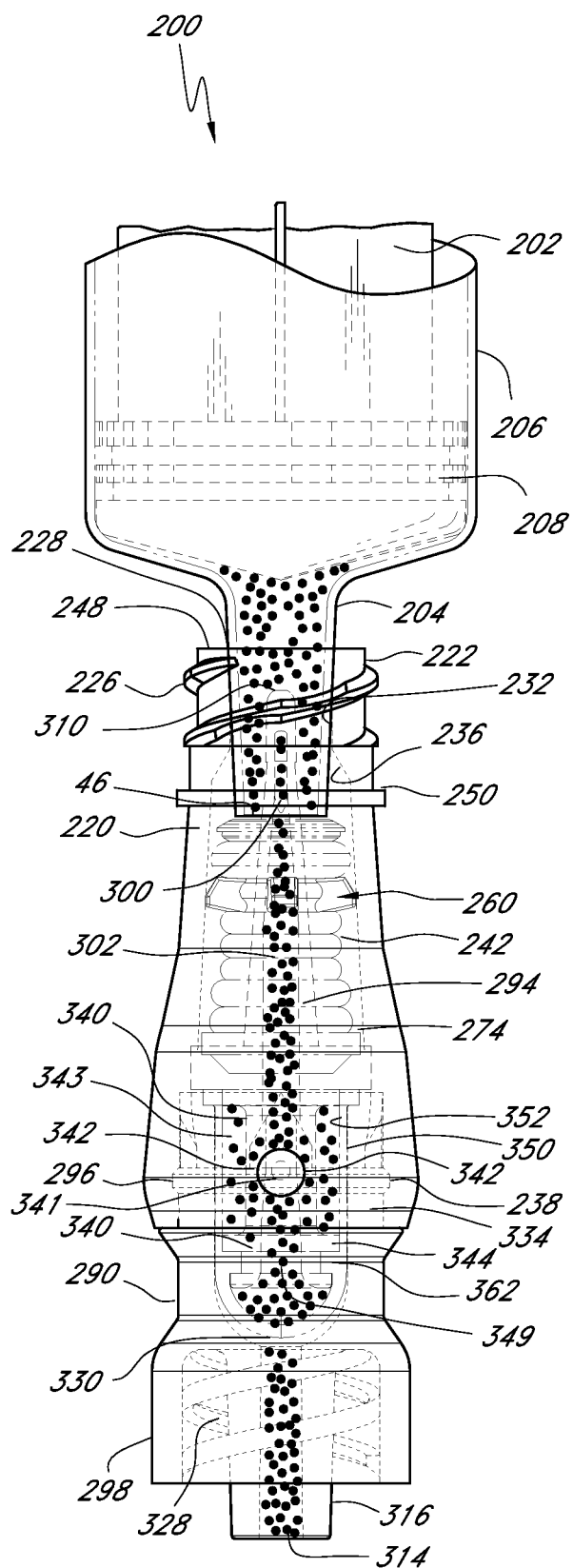
FIG. 17A is a front view of the embodiment of the connector shown in FIG. 11A, showing the seal member in an open position, the plunger of the syringe advanced to the bottom surface of the syringe, and fluid flow visible through the transparent wall of the body, seal, and support.
Figure 19:
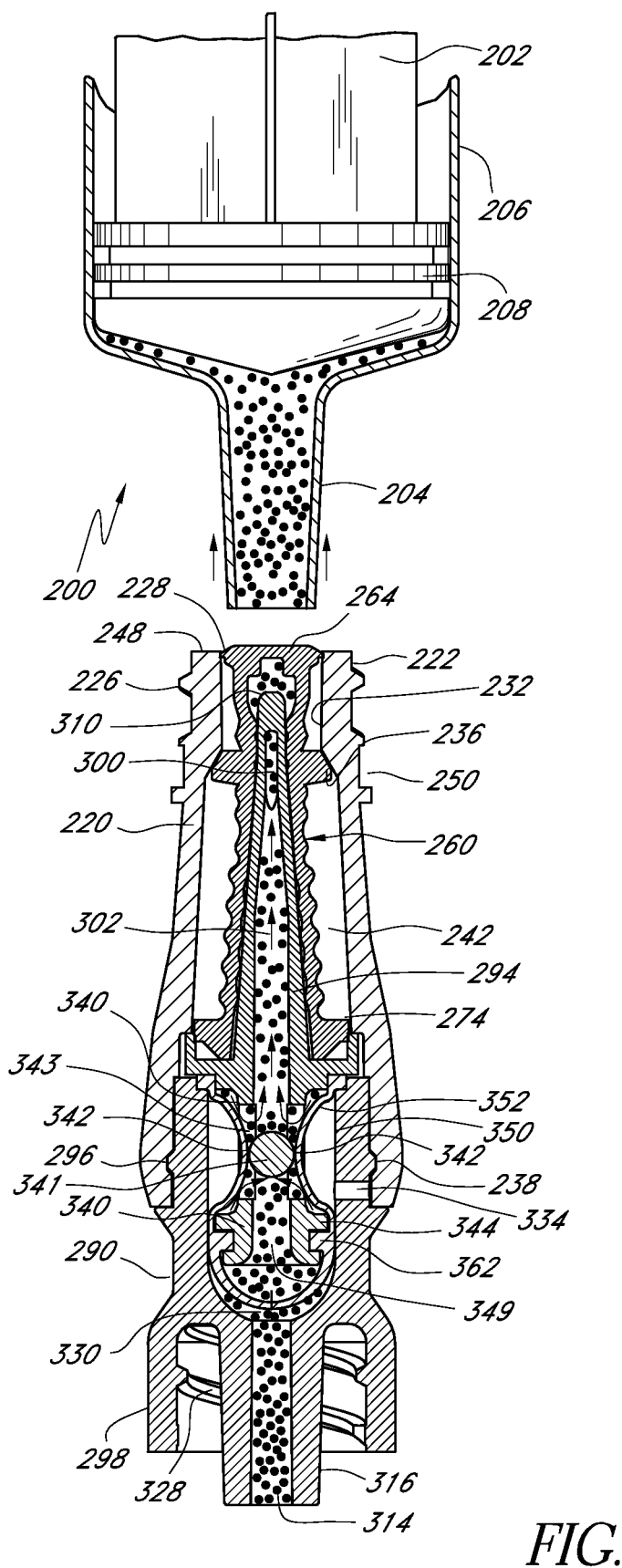
FIG. 19 is a section view of the embodiment of the connector shown in FIG. 11A, showing the seal member in the first position after the syringe has been removed from the connector.
Figure 19A:
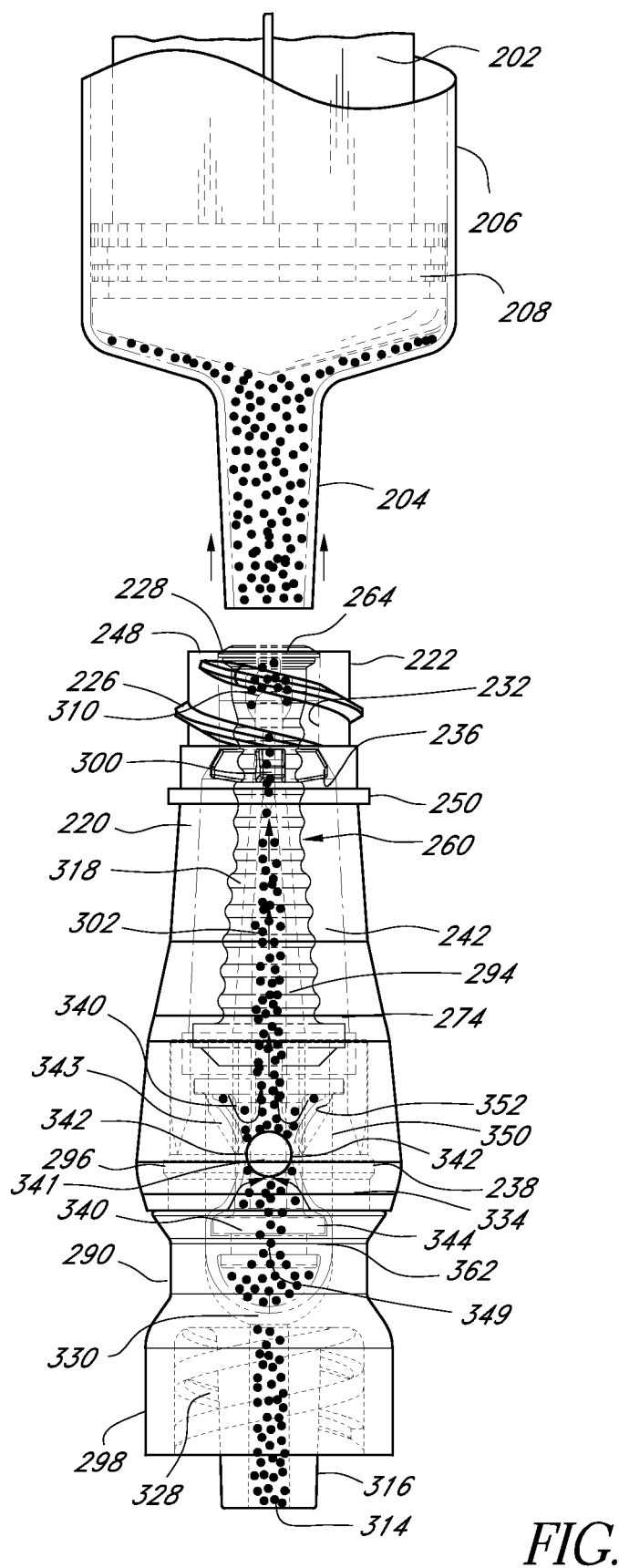
FIG. 19A is a front view of the embodiment of the connector shown in FIG. 11A, showing the seal member in the first position after the syringe has been removed from the connector and fluid in the connector visible through the transparent wall of the body, seal, and support.

With reference to FIGS. 15-19, the operation of an embodiment of connector 210 is illustrated in a manner similar to FIGS. 6-10A and the connector 10. FIG. 15 illustrates the position of the components comprising the connector 210 when the seal member 260 is biased in the closed position, e.g., before a syringe or other medical implement has been joined with, or inserted into, the connector 210. FIGS. 18 and 19 illustrate the thin walls of the regulator 350 deflecting radially inward within the volume 343 under the vacuum pressure effect resulting from the springback of the syringe 200 rubber seal 208. The thin walls deflect to absorb the pressure differential, insulating the fluid on the distal side of the slits 360 from the resultant vacuum.

Figure 20:
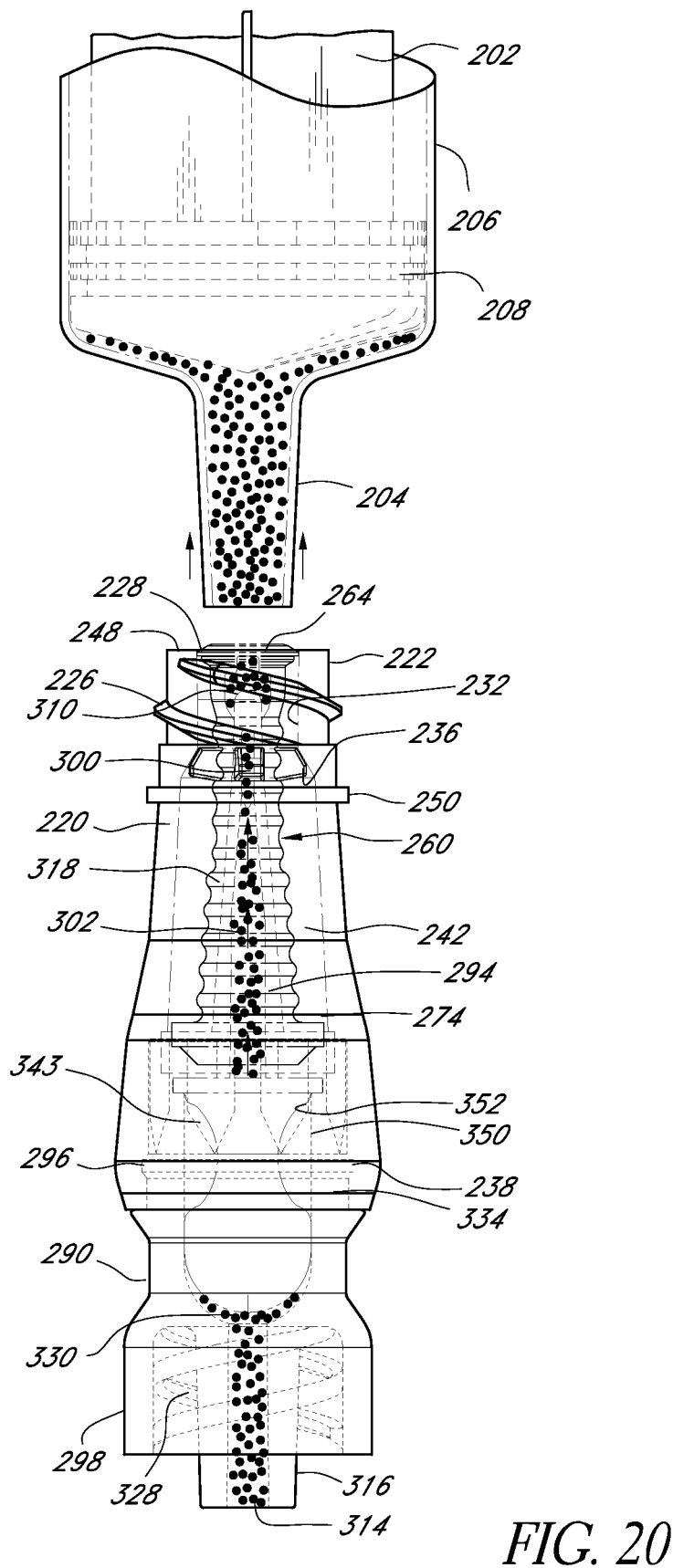
FIG. 20 is a front view of another embodiment of a connector showing a seal member in a first position after a syringe has been removed from the connector and fluid has been injected through the connector, wherein fluid in a portion of the connector is visible.
Figure 21:
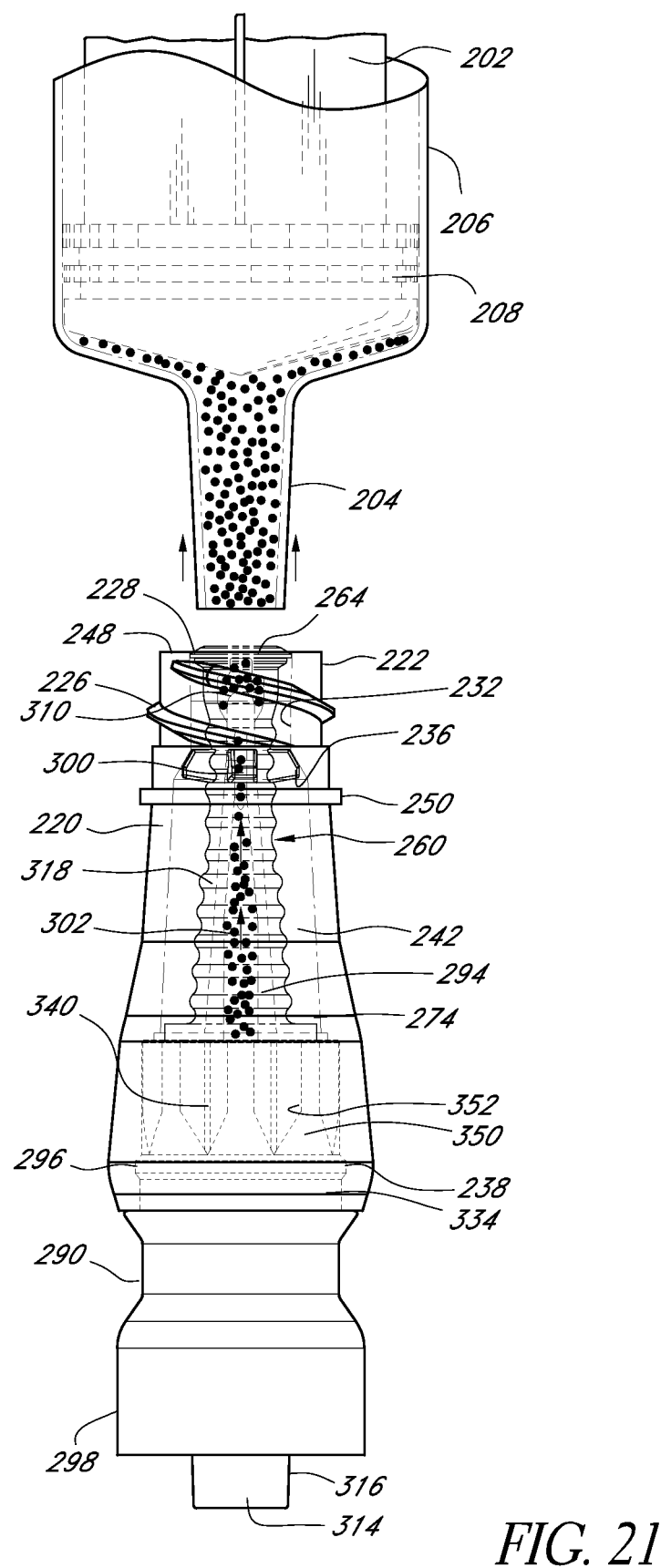
FIG. 21 is a front view of another embodiment of a connector showing a seal member in a first position after a syringe has been removed from the connector and fluid has been injected through the connector, wherein fluid in a portion of the connector is visible.

With reference to FIGS. 20 and 21, embodiments of the connector 210 are shown having various features of the distal end of the connector made of opaque material. FIG. 20 shows the regulator 350 with an opaque material such that the internal fluid is not visible. FIG. 21 shows the base 290 having an opaque material such that all of the internal features and fluid are not visible from the external side or surface of the connector 210 at the base 290. The base 290 and/or the regulator 350 can be an opaque material to prevent the fluid flow path within the volume 343 from being visible to the practitioner and avoid confusion that might result from misinterpretation of the fluid presence in the volume 343. The fluid can be intended to be present in the volume 343 to absorb and dampen pressure differential and prevent backflow conditions into the connector 210, and not necessarily an indicator of fluid leak or connector 210 malfunction. Nevertheless, fluid is visible through a substantial portion of the connector with this opaque feature. In some embodiments, a rigid internal flow path is visible through a substantial portion of the connector, and in particular in the central portion of the connector wherein the walls are configured to permit a relatively clear view of the internal flow path.

Although some specific examples have been provided herein, it should be understood that a transparent connector and/or backflow resistance module can be incorporated into many other types of medical implements and/or connectors than those specifically disclosed herein. For example, a backflow resistance module can be incorporated into a y-site connector, or into a connector providing access to an IV bag or other medication container, or into a catheter line.

Any features of the embodiments shown and/or described in the figures that have not been expressly described in this text, such as distances, proportions of components, etc. are also intended to form part of this disclosure. Additionally, although these inventions have been disclosed in the context of various embodiments, features, aspects, and examples, it will be understood by those skilled in the art that embodiments of the present invention extend beyond the specifically disclosed embodiments to other alternative embodiments and/or uses of the invention and obvious modifications and equivalents thereof. Accordingly, it should be understood that various features and aspects of the disclosed embodiments can be combined with, or substituted for, one another in order to perform varying modes of the disclosed inventions. Thus, it is intended that the scope of the present invention disclosed herein should not be limited by the particular disclosed embodiments described herein.

What is claimed is:

1. A medical connector for use in a fluid pathway, the connector comprising:
    a housing having a proximal end with a proximal opening and a distal end with a distal male luer opening, a cavity extending therebetween, and configured to be transparent such that the cavity is visible through the housing;
    a valve member having an interior cavity, said valve member disposed within the housing and configured to be transparent such that the interior cavity is visible through the valve member, and said valve member further having a proximal end that substantially fills the housing proximal opening and includes a proximal opening that is biased closed to obstruct fluid flow therethrough, wherein the valve member is configured to selectively seal the housing proximal opening and to obstruct fluid communication between the housing proximal end and the housing distal end when the valve member is in a first position and to establish fluid communication between the housing proximal end and the housing distal end when the valve member is in a second position; and
    a support member configured to be received within the valve member, said support member having an inner conduit that extends from adjacent a proximal tip portion having at least one opening that extends through the support member to the inner conduit to a distal end of the support member, and is configured to selectively establish fluid communication between the housing proximal end and the housing distal end, wherein the fluid communication between the housing proximal end and the housing distal end is established when the tip portion and opening protrude through the valve proximal opening and the valve member is provided in the second position and at least a portion of the opening is positioned proximal to the valve member proximal opening, wherein said support member is configured to be transparent such that the inner conduit is visible through the support member; and
    wherein a fluid flow path establishing the fluid communication between the housing proximal end and the housing distal end is visible through at least a portion of each of the transparent housing, the transparent valve member, and the transparent support member, and wherein the fluid flow path within the inner conduit of the support member from the proximal end of the valve member when the valve member is in the second position to the housing distal end is narrower than the outer diameter of the distal end at the male luer opening.

2. The medical connector of claim 1, wherein the valve member sealingly engages internal surfaces of the housing cavity.

3. The medical connector of claim 1, wherein the valve member fills the housing cavity such that it obstructs entry of contamination into the housing cavity.

4. The medical connector of claim 1, wherein the valve member further comprises a radially outwardly extending protrusion.

5. The medical connector of claim 4, further comprising a protrusion disposed on an inner surface of the housing cavity, wherein the valve member outward protrusion engages the housing protrusion.

6. The medical connector of claim 5, wherein the engagement between the outward protrusion and the housing protrusion positions the valve member proximal end co-planar with the housing proximal end.

7. The medical connector of claim 1, wherein the housing comprises a body and a base, and a portion of the body overlaps a portion of the base.

* * * * *